United States Patent
Albaghdadi et al.

(10) Patent No.: US 9,427,433 B2
(45) Date of Patent: Aug. 30, 2016

(54) METHODS AND COMPOSITIONS FOR ENHANCING FERTILITY AND/OR INHIBITING PREGNANCY FAILURE AND RESTORING GLUCOSE TOLERANCE

(75) Inventors: Ahmad J. H. Albaghdadi, Kingston (CA); Frederick W. K. Kan, Kingston (CA)

(73) Assignee: Queen's University at Kingston, Kingston, Ontario (CA)

( * ) Notice: Subject to any disclaimer, the term of this patent is extended or adjusted under 35 U.S.C. 154(b) by 93 days.

(21) Appl. No.: 14/122,555

(22) PCT Filed: May 31, 2012

(86) PCT No.: PCT/CA2012/000506
§ 371 (c)(1),
(2), (4) Date: Nov. 26, 2013

(87) PCT Pub. No.: WO2012/162796
PCT Pub. Date: Dec. 6, 2012

(65) Prior Publication Data
US 2014/0113928 A1   Apr. 24, 2014

Related U.S. Application Data

(60) Provisional application No. 61/519,848, filed on May 31, 2011, provisional application No. 61/558,586, filed on Nov. 11, 2011.

(51) Int. Cl.
*A01N 43/42* (2006.01)
*A61K 31/44* (2006.01)
*A61K 31/439* (2006.01)
*A61K 31/436* (2006.01)

(52) U.S. Cl.
CPC ........... *A61K 31/439* (2013.01); *A61K 31/436* (2013.01)

(58) Field of Classification Search
USPC ...................................................... 514/291
See application file for complete search history.

(56) References Cited

FOREIGN PATENT DOCUMENTS

WO    WO 2004/026333 A1    4/2004

OTHER PUBLICATIONS

Platt et. al. (Diabet. Med. (2002) 19:216-220).*
Murase et. al. (Diabetes (1990) 39:1584-1586).*
Carrol et. al. (Transplant. Proc. (1991) 23:3351-3353).*
Miyagawa et. al. (Diabetologia (1990) 33:503-505).*
Kurasawa et. al. (Clinical Immunology and Immunopathology (1990) 57:274-279).*
Anisimov et al. "Rapamycin Extends Maximal Lifespan in Cancer-Prone Mice" The American Journal of Pathology 2010 176(5):2092-2097.
Carroll et al. "The Use of FK 506 in New-Onset Type I Diabetes in Man" Transplantation Proceedings 1991 23(6):3351-3353.
Jain et al. "Pregnancy After Liver Transplantation Under Tacrolimus" Transplantation 1997 64(4):559-565.
Kurasawa et al. "The Immunosuppressant FK-506 Prevents Progression of Diabetes in Nonobese Diabetic Mice" Clinical Immunology and Immunopathology 1990 57:274-279.
Laifer, S.A. and Guido, R.S. "Reproductive Function and Outcome of Pregnancy After Liver Transplantation in Women" Mayo Clinic Proceedings 1995 70:388-394.
Miyagawa et al. "Preventative Effect of a New Immunosuppressant FK-506 on Insulitis and Diabetes in Non-Obese Diabetic Mice" Diabetologia 1990 33:503-505.
Murase et al. "Effect of FK 506 on Spontaneous Diabetes in BB Rats" Diabetes 1990 39:1584-1586.
Madsen et al. "FK506 Increases Permeability in Rat Intestine by Inhibiting Mitochondrial Function" Gastroenterology 1995 109:107-114.
Tsang et al. "Targeting Mammalian Target of Rapamycin (mTOR) for Health and Diseases" Drug Discovery Today 2007 12(3/4):112-124.
International Search Report from PCT/CA2012/000506, Sep. 12, 2012, PCT.
International Preliminary Report on Patentability from PCT/CA2012/000506, Dec. 12, 2013, PCT.
Cravedi et al. "Sirolimus for Calcineurin Inhibitors in Organ Transplantation: contra" Kidney International 2010 78:1068-1074.
Larsen et al. "Tacrolimus and Sirolimus Cause Insulin Resistance in Normal Sprague Dawley Rats" Transplantation 2006 82(4):466-470.
Ollech et al. "Post-transplant Diabetes Mellitus in Lung Transplant Recipients: Incidence and Risk Factors" European Journal of Cardio-thoracic Surgery 2008 33:844-848.
Tsang et al. "Targeting Mammalian Target of Rapmycin (mTOR) for Health and Diseases" Drug Discovery Today 2007 12(3/4):112-124.

* cited by examiner

*Primary Examiner* — Marcos Sznaidman
(74) *Attorney, Agent, or Firm* — Licata & Tyrrell P.C.; Carol Miernicki; Angela P. Lyon

(57) ABSTRACT

Methods and compositions for enhancing fertility and/or inhibiting pregnancy failure, restoring glucose tolerance and/or preventing glucose intolerance and/or maintaining glucose homeostasis and/or inducing or enhancing weight loss, treating dyslipidemia, treating hypertestosteronism or hyperandrogenism, and/or treating type 2 diabetes in an individual in need thereof are provided. These involve compositions that inhibit expression of interferon-gamma (IFN-γ) or a downstream IFN-γ-stimulated gene, which is preferably a macrolide immunosuppressant compound.

8 Claims, 34 Drawing Sheets

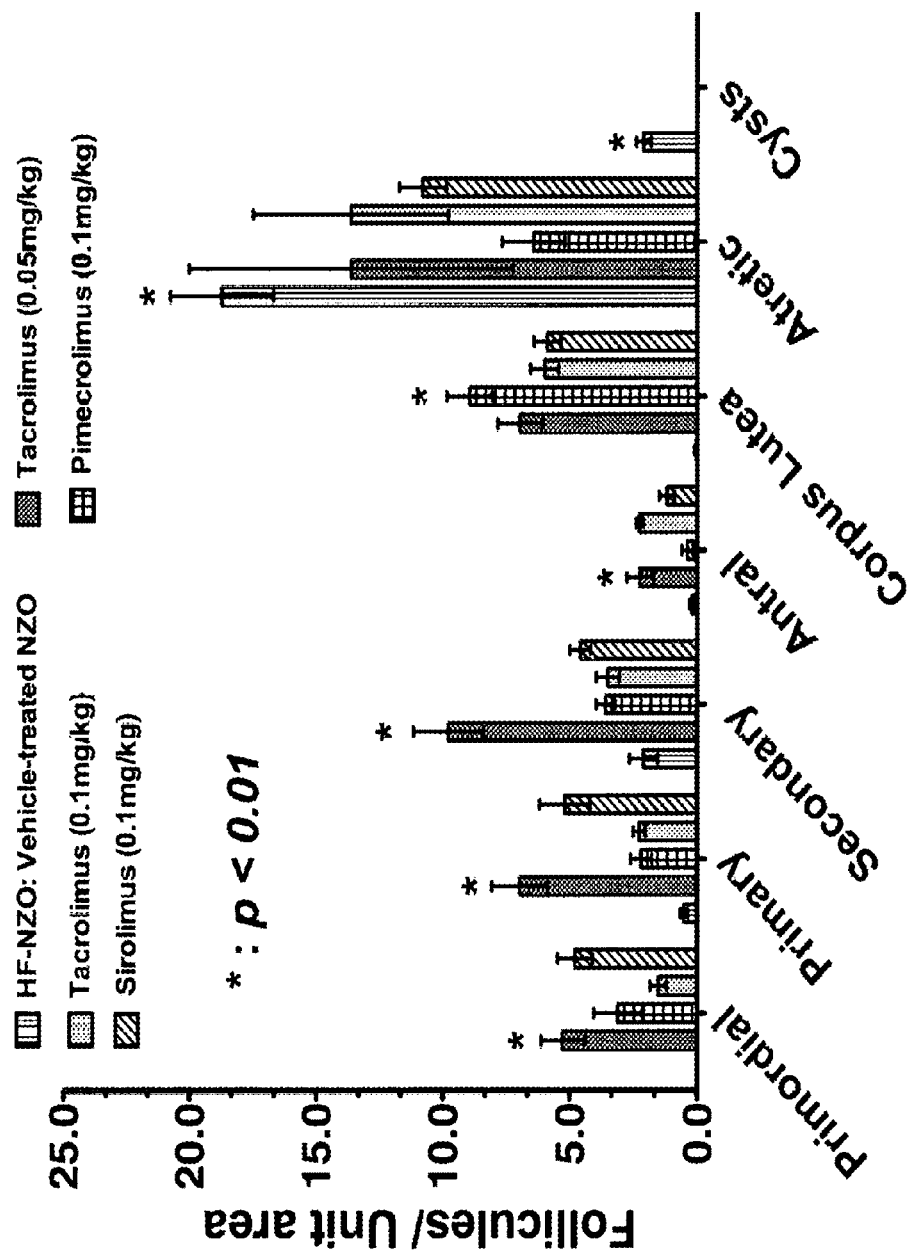
FIG. 3D (ii)

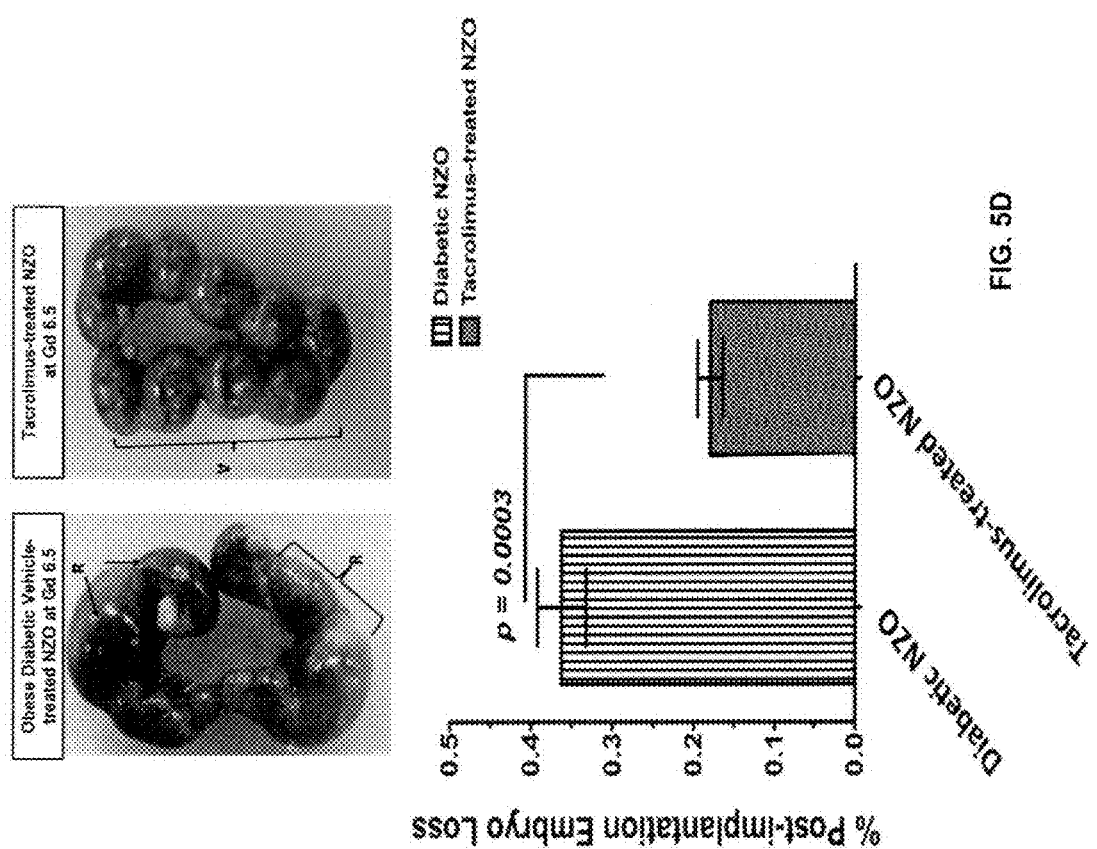

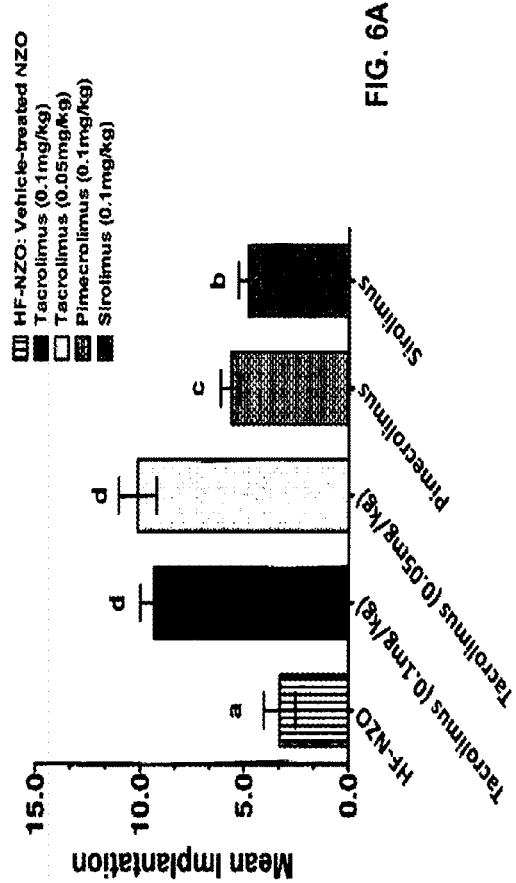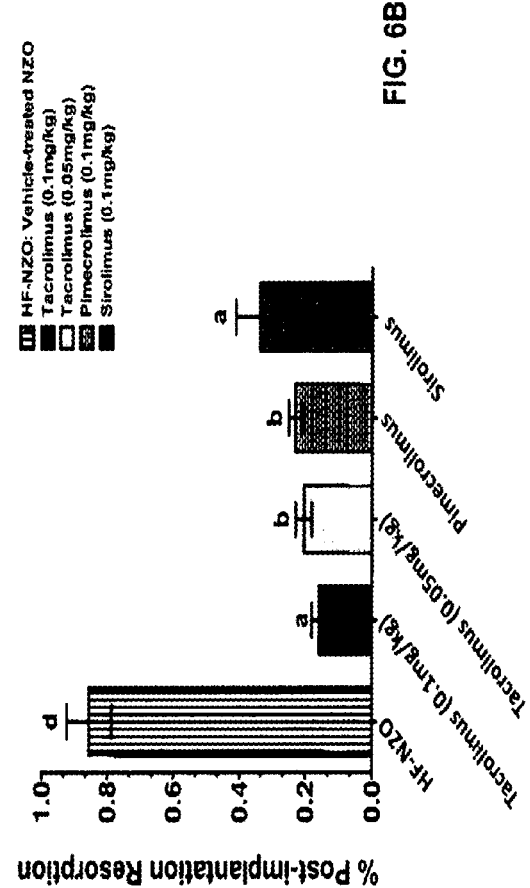
FIG. 6A
FIG. 6B

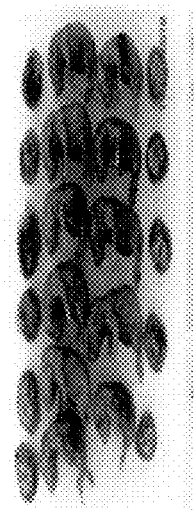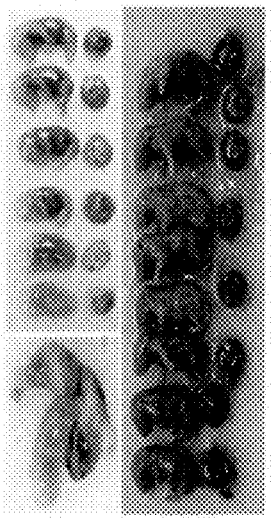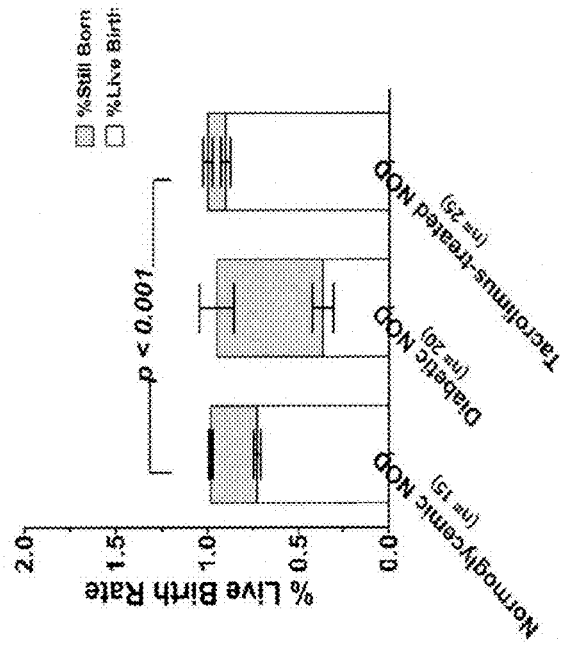
FIG. 13A
FIG. 13B
FIG. 13C
FIG. 13F

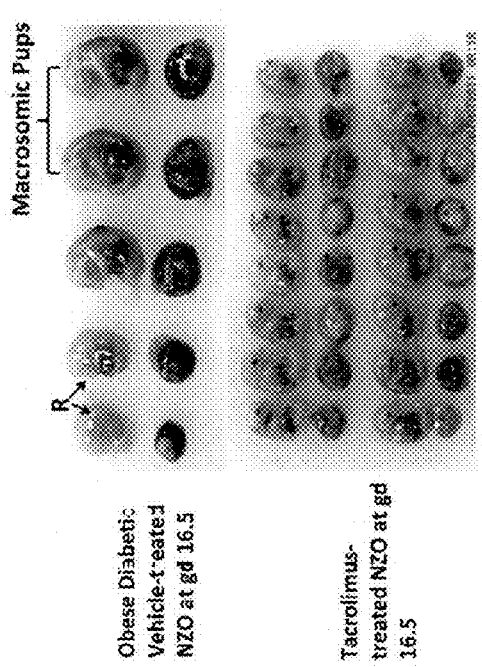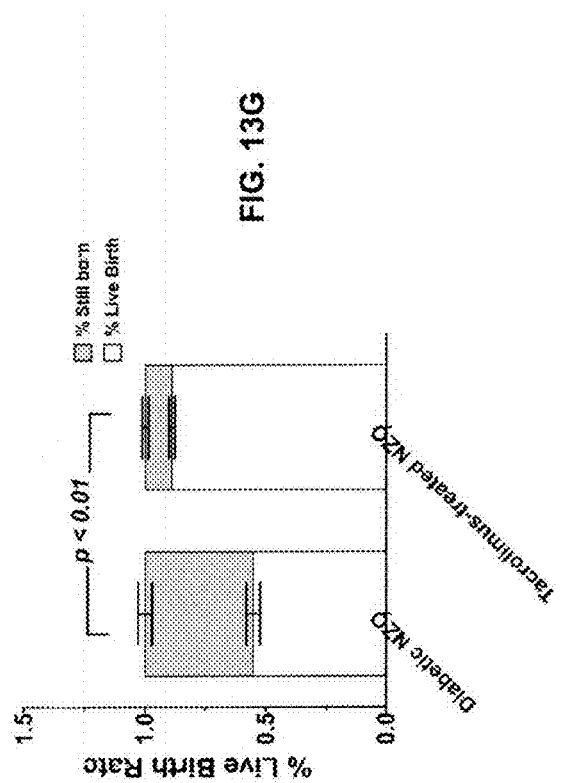

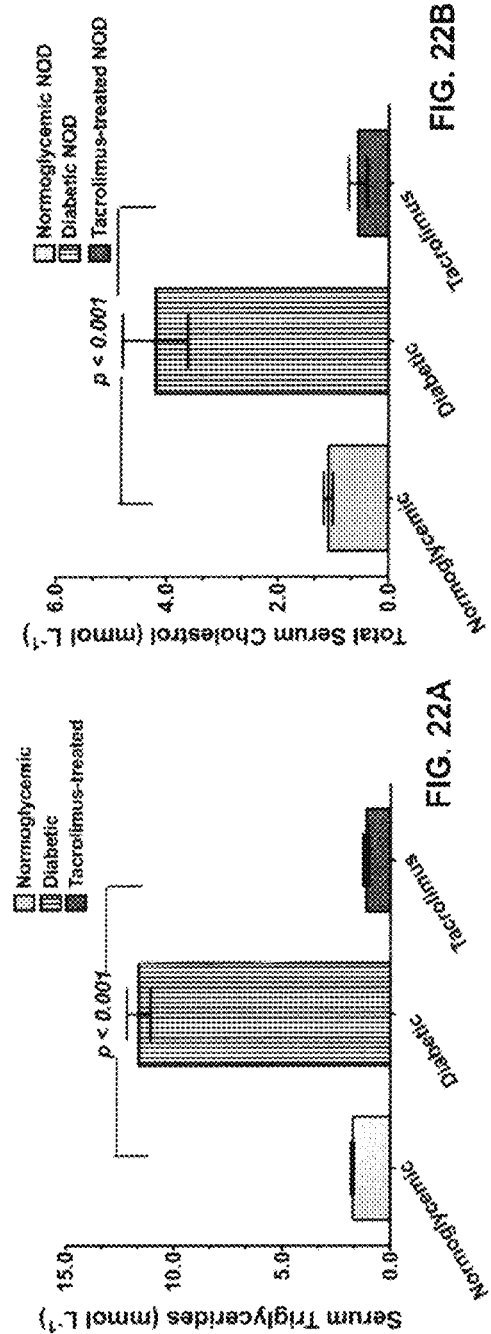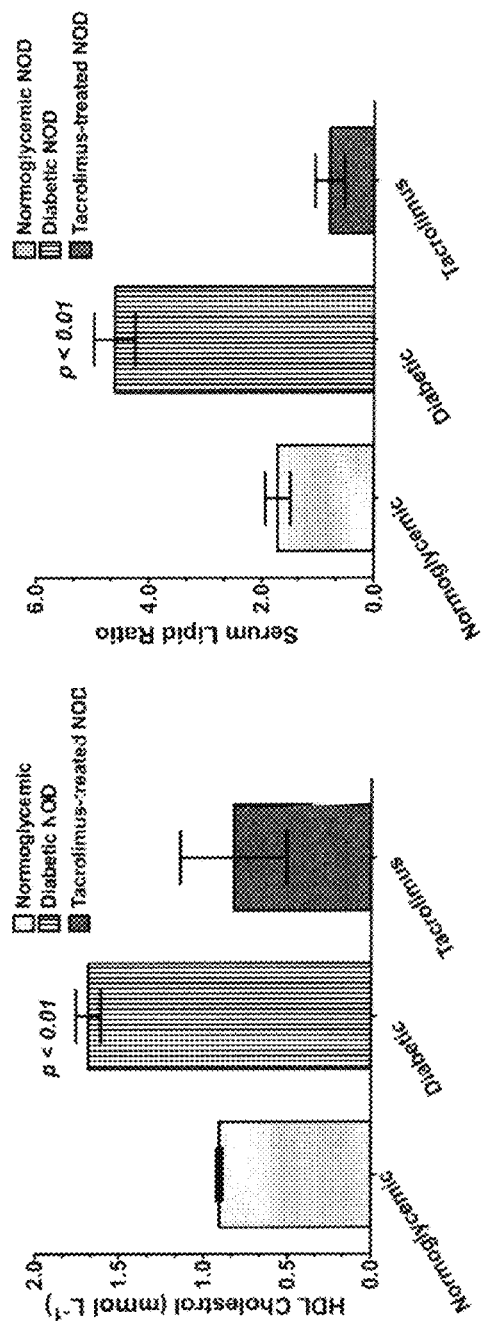
FIG. 22A
FIG. 22B
FIG. 22C
FIG. 22D

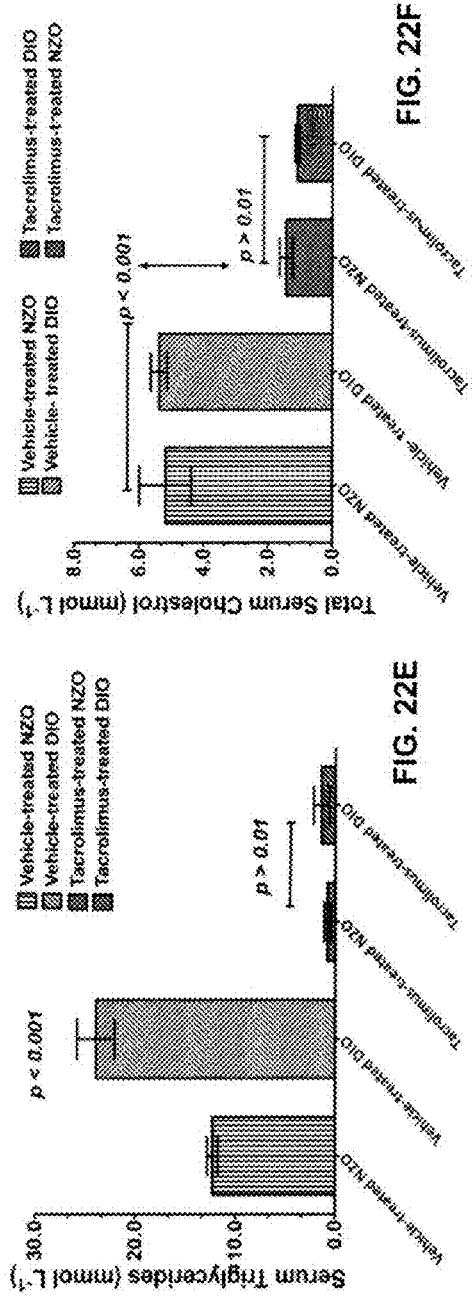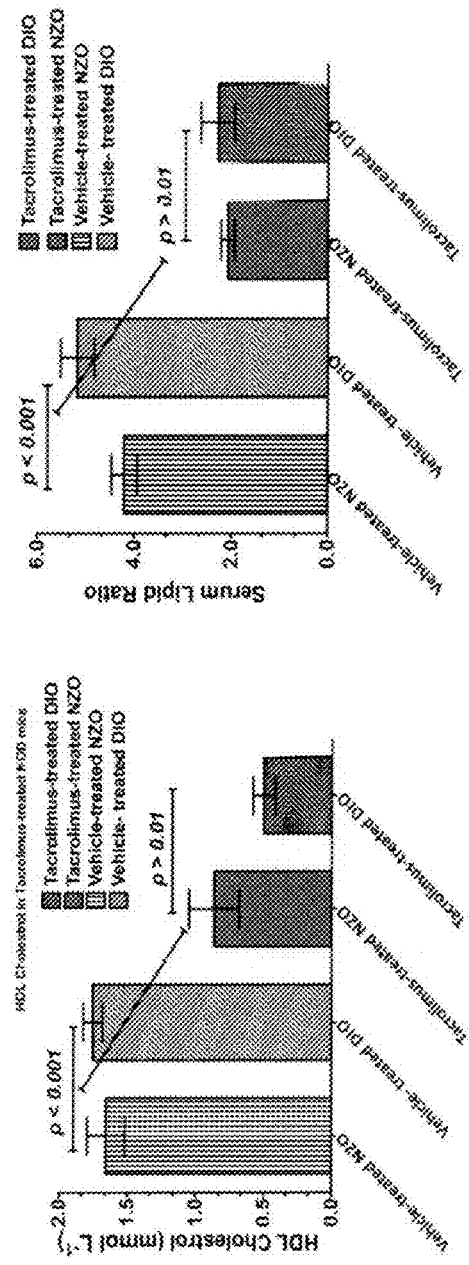

a flow chart showing the experimental design

METHODS AND COMPOSITIONS FOR ENHANCING FERTILITY AND/OR INHIBITING PREGNANCY FAILURE AND RESTORING GLUCOSE TOLERANCE

This patent application claims the benefit of priority from U.S. Provisional Application Ser. No. 61/558,586, filed Nov. 11, 2011 and U.S. Provisional Application Ser. No. 61/519,848, filed May 31, 2011, the contents of each of which are hereby incorporated by reference in their entirety.

FIELD OF THE INVENTION

The present invention relates to methods and compositions for enhancing fertility and/or inhibiting pregnancy failure in an individual in need thereof. The present invention is also related to methods and compositions for restoring glucose tolerance and/or preventing glucose intolerance and/or maintaining glucose homeostasis and/or increasing insulin sensitivity and/or treating type 2 diabetes and/or preventing weight gain and/or inducing or enhancing weight loss and/or treating dyslipidemia in an individual in need thereof. The present invention is also related to methods and compositions for treating hypertestosteronism or hyperandrogenism.

BACKGROUND OF THE INVENTION

Tacrolimus or FK-506, the active ingredient in PROGRAF (tacrolimus capsules and injections, Astellas Pharma US, Inc. Deerfield, Ill.), is a macrolide immunosuppressant produced from *Streptomyces tsukubaensis*. Tacrolimus is used along with other medications to prevent rejection (attack of a transplanted organ by the immune system of a person receiving the organ) in people who have received kidney, liver, or heart transplants. Tacrolimus is in a class of medications called immunosuppressants. It works by decreasing the activity of the immune system to prevent it from attacking the transplanted organ. Tacrolimus has been found to be a safe drug for use during pregnancy in transplant patients (Laifer. S. A. and Guido, R. S. Mayo Clin Proc (1995) 70:38894; Jain et al. Transplantation (1997) 64:55965). Tacrolimus (FK506) has been shown to suppress overt diabetes in 84% of treated NOD mice, a model for Type 1 diabetes, at younger age (Kurasawa et al. Clin Imm Immuno Ther (1990) 57:274-279). In 1991, a clinical study with tacrolimus (0.15 mg/kg BID) was initiated in patients with type I diabetes (Carroll et al., Transplant Proc. 1991 December; 23(6):3351-3). While the initial response of five patients was disclosed as "encouraging" (Carroll et al., Transplant Proc. 1991 December; 23(6):3351-3), published results were inconclusive and no further data from this clinical study or further clinical studies have been published.

SUMMARY OF THE INVENTION

An aspect of the present invention relates to a method for enhancing fertility and/or inhibiting pregnancy failure in an individual in need thereof.

In one embodiment, the individual is administered a composition which inhibits expression of interferon-gamma (IFN-γ) or a downstream IFN-γ-stimulated gene.

In one embodiment, the individual is administered a macrolide immunosuppressant.

In one embodiment, the individual is administered tacrolimus, pimecrolimus or sirolimus.

In one embodiment, the individual is administered tacrolimus.

In one embodiment, the individual has polycystic ovarian syndrome.

Another aspect of the present invention relates to a composition for enhancing fertility and/or inhibiting pregnancy failure in an individual in need thereof.

In one embodiment, the composition comprises an effective amount of a pharmaceutically active ingredient which inhibits interferon-gamma (IFN-γ) or a downstream IFN-γ-stimulated gene.

In one embodiment, the composition comprises a macrolide immunosuppressant.

In one embodiment, the composition comprises tacrolimus, pimecrolimus or sirolimus.

In one embodiment, the individual is administered tacrolimus.

Another aspect of the present invention relates to a method of restoring glucose tolerance and/or preventing glucose intolerance and/or maintaining glucose homeostasis and/or increasing insulin sensitivity and/or treating type 2 diabetes and/or preventing weight gain and/or inducing or enhancing weight loss and/or treating dyslipidemia in an individual in need thereof.

In one embodiment, the individual is administered a composition which inhibits interferon-gamma (IFN-γ) or a downstream IFN-γ-stimulated gene.

In one embodiment, the individual is administered a macrolide immunosuppressant.

In one embodiment, the individual is administered tacrolimus, pimecrolimus or sirolimus.

In one embodiment, the individual is administered tacrolimus.

In one embodiment, the individual is obese and/or suffers from type 1 or type 2 diabetes.

Another aspect of the present invention relates to a method for treating hypertestosteronism or hyperandrogenism in an individual in need thereof.

In one embodiment, the individual is administered a composition which inhibits interferon-gamma (IFN-γ) or a downstream IFN-γ-stimulated gene.

In one embodiment, the individual is administered a macrolide immunosuppressant.

In one embodiment, the individual is administered tacrolimus, pimecrolimus or sirolimus.

In one embodiment, the individual is administered tacrolimus.

Another aspect of the present invention relates to a method for treating type 2 diabetes in an individual in need thereof.

In one embodiment, the individual is administered a composition which inhibits interferon-gamma (IFN-γ) or a downstream IFN-γ-stimulated gene.

In one embodiment, the individual is administered a macrolide immunosuppressant.

In one embodiment, the individual is administered tacrolimus, pimecrolimus or sirolimus.

In one embodiment, the individual is administered tacrolimus.

BRIEF DESCRIPTION OF THE FIGURES

FIG. 4A) and low serum levels of luteinizing hormone (LH; FIG. 4B), cardinal biochemical features of established PCOS syndrome. Data are represented as mean±SEM. N=3.

FIGS. 5A through 5D show results of short-term administration of tacrolimus enhancing implantation rate (compare photomicrographs in FIG. 5A and their corresponding graph bars) and supporting post-implantation embryo development, promoting early pregnancy progression and reducing rates of embryonic and fetal resorption in all treated mated mice (compare photomicrographs in FIG. 5B and their corresponding graph bars). Representative photomicrographs of implantation sites obtained during pregnancy days 4.5 and day 6.5 from tacrolimus treated diabetes prone NOD mice and type 2 diabetic NZO mice versus their vehicle treated diabetic NOD and NZO mice are depicted in FIGS. 5A and 5B and 5C and 5D, respectively. Resorbed implantation sites are marked with the letter "R". V marks viable implantation sites.

FIGS. 6A and 6B show results demonstrating short-term macrolide administration enhances implantation rate of NZO mice fed a high fat diet (60% calories from fat). In these experiments, tacrolimus (0.05 and 0.1 mg/kg), pimecrolimus (0.1 mg/kg) and sirolimus (0.1 mg/kg) administered subcutaneously every other day for three weeks significantly improved implantation rate (p<0.05) compared to vehicle-treated control female mice. The same treatments also significantly reduced embryonic and fetal absorption rate compared to vehicle-treated controls (p<0.05). While all of the macrolides tested were effective at enhancing fertility, tacrolimus had greater comparative effects.

FIGS. 13A through 13G show results of short term administration of tacrolimus reducing the rates of stillbirths and malformations associated with the diabetic gestation and restoration of normal term pregnancy with high rate of live births in the treated diabetic and obese mice. Numbers and external morphological features of near term (Gd.16.5) pups delivered to tacrolimus-treated versus those delivered to vehicle-treated diabetic and their normoglycemic control mice are depicted in FIGS. 13A through 13C, respectively. Fetal viability rates and external features of pups delivered to diabetic and obese mice with those of the tacrolimus-treated obese and type 2 diabetic mice are depicted in FIGS. 13D and 13E, respectively. Graph bars of FIGS. 13F and 13G display figure statistics.

FIGS. 22A to 22H show results of tacrolimus restoring normal lipid profile in all treated diabetic and obese mice fed with 60% fat for 12 weeks. Normal serum levels of Triglycerides (FIG. 22A and FIG. 22B), Total Cholesterol (FIG. 22C and FIG. 22D), High-density Lipoprotein (HDL) Cholesterol (FIG. 22E and FIG. 22F) and lipid Ratio representing the overall lipid profile (FIG. 22G and FIG. 22H) were obtained after the administration of tacrolimus to the diabetic and obese mice despite their continued high fat calorie intake. Blood samples were taken at day 4.5 post-coitum and values on the Y-axis are plotted as power of 10.

DETAILED DESCRIPTION OF THE INVENTION

Figure 1:
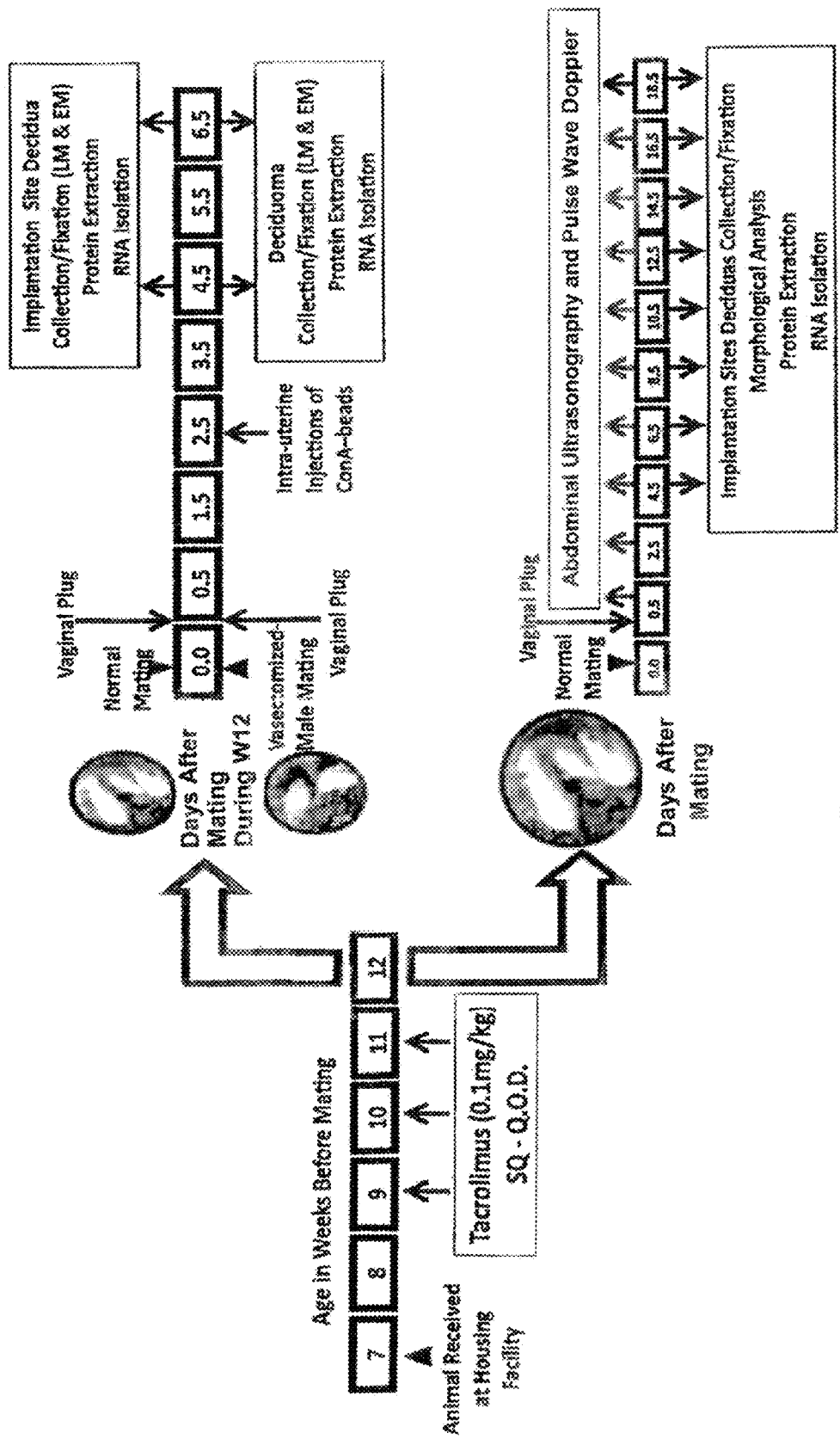
FIG. 1 is a flow chart showing the experimental design and dosing schedule for tacrolimus used in NOD mice, a model for Type 1 diabetes.

Early pregnancy failure, repeated miscarriages and a wide spectrum of intrauterine growth restriction (IUGR) are common fecundity problems. These problems are exacerbated in autoimmune individuals.

At the child-bearing reproductive age, diabetic women are generally less fertile than their non-diabetic controls. High rates of recurrent miscarriages and still births, increased risk of development of mid- to late-autoimmune and vascular pregnancy-related complications (such as gestational hypertension and preeclampsia) accompanied by high occurrence of congenital malformations and neonatal and post-neonatal deaths constitute the hallmark of fecundity problems in fertile diabetic individuals (Platt et al. Diabet Med (2002) 19(3): 216-220; Casson et al. BMJ (1997) 315:275-278). Inherited aberrant autoimmune activation of the T-cell receptors in autoimmune diabetic individuals is believed to initiate the autoimmune destructive cascades that result in the disease progression (Green, E. A. and Flavell, R. A. Curr Opin Immunol (1999) 11:663-669). In an Autoimmune Non-Obese Diabetic (NOD) mouse model, gestational endometrium exhibited immune and vascular defects that were suggested to likely contribute to murine fetal loss and birth defects (Burke et al. Diabetes (2007) 56:2919-2926). Based upon these experiments in mice it has been suggested that analogous problems and preeclampsia in diabetic women may involve similar mechanisms (Burke et al. Diabetes (2007) 56:2919-2926).

A normal pregnancy is a pro-inflammatory condition that requires a distinct endogenous modification via a counter-regulatory local uterine anti-inflammatory immune response (Th2) mediated by "immune" conditioned local antigen presenting cells (APCs) required for its normal progression (Germain et al. Immunol (2007) 178:5949-5956). Failure of the maternal immune response to convert to the Th2 immune cytokine profile during gestation is commonly seen among women who are genetically susceptible to autoimmune complicated pregnancies (Germain et al. J Immunol (2007) 178:5949 5956). Interferon Gamma (IFN-γ) plays an integral role in priming immunological responses of the antigen presenting cells in a manner that determines their Th1/Th2 committed responses (Boehm et al. Annu Rev Immunol (1997) 15:749-795). Aberrant uterine/decidual production of IFN-γ is constitutively observed in the Non-Obese Diabetic mice (Burke et al. Diabetes (2007) 56:2919-2926; Albaghdadi et al. Biol. Reprod. (Apr. 25 2012) DOI:10.1095/biolreprod.112. 100016), a mouse model of the human autoimmune diabetes mellitus, which also mimics situation in women with a history of recurrent spontaneous abortions as well as those with preeclampsia (Palfi et al. Am J Reprod Immunol (1999) 41(4):257-63; N G et al. Am J Reprod Immunol (2002) 48(2):77-86; Daniel et al. J Reprod Immunol (2002) 54(1):133-142). IFN-γ expression has been disclosed to be central in initiation of pregnancy-induced uterine arterial remodeling (Ashkar et al. J Exp Med (2000) 192:259-270). However, it has been found that high level expression of IFN-γ is detrimental to embryo implantation at the initiation of pregnancy (Albaghdadi et al. Biol. Reprod. (Apr. 25 2012) DOI:10.1095/biolreprod.112.100016). IFN-γ has also been found to inhibit extravillous trophoblast (EVT) cell invasion required for successful pregnancy (Karmakar et al. J Biol Chem (2004) 279:55297-55307; Lash et al. FASEB J (2006) 20:2512-2518).

Maintaining adequate glucose homeostasis with insulin supplement is thus far the most widely used therapeutic approach in the care of pregnant diabetic women.

The present invention provides methods and compositions for enhancing fertility and/or inhibiting pregnancy failure in individuals in need thereof.

For purposes of the present invention, by "enhancing fertility and/or inhibiting pregnancy failure" it is meant to encompass, but is not limited to, restoring normal pregnancy patterns, increasing fertility, stimulating ovulation, increasing implantation of embryos and/or treating defective uterine receptivity in an individual in need thereof.

In this embodiment, by "individual in need thereof" or "individuals in need thereof" it is meant to be inclusive of any woman suffering from infertility and/or one or more previous pregnancy failures. Examples of such individuals include, but are not limited to, women with recurrent spontaneous abortion including those with and without diabetes, women with polycystic ovary syndrome (PCOS), endometriosis, or gestational diabetes and women at higher risk of developing hemolysis-low platelet-pre-eclampsia syndrome.

In one embodiment of the method, the individual in need thereof has an autoimmune condition. In one embodiment the individual is hyperglycemic. In one embodiment, the individual is pre-diabetic. In one embodiment, the individual has type 1 diabetes. In another embodiment, the individual has type 2 diabetes. In another embodiment, the individual has impaired fasting glycemia.

In one embodiment, the individual in need thereof is obese.

The present invention also provides methods and compositions for restoring glucose tolerance and/or preventing glucose intolerance, maintaining glucose homeostasis and/or increasing insulin sensitivity and/or preventing weight gain and/or inducing or enhancing weight loss and/or treating dyslipidemia in an individual in need thereof. In this embodiment, an individual in need thereof is one suffering from glucose intolerance and/or undesirable weight gain. Examples of such individuals include, but are not limited to, those who are obese and/or those suffering from type 1 diabetes or type 2 diabetes and/or who are pregnant and/or who have gestational diabetes.

The present invention also provides methods for treating hypertestosteronism or hyperandrogenism in individuals in need thereof and methods for treating type 2 diabetes in individuals in need thereof.

In one embodiment of the present invention, the individual in need is administered an effective amount of a pharmaceutically active ingredient which inhibits expression of interferon-gamma (IFN-γ) or a downstream IFN-γ-stimulated gene. In one embodiment, the pharmaceutically active ingredient is a macrolide immunosuppressant. In one embodiment, the pharmaceutically active ingredient is tacrolimus. As will be understood by the skilled artisan upon reading this disclosure, however, alternative macrolide immunosuppressants can also be used. Nonlimiting examples include sirolimus (Rapamycin) and pimecrolimus (Elidel). Accordingly, in another embodiment, the pharmaceutically active ingredient is pimecrolimus or sirolimus. The term "effective amount" encompasses the term "dose" or "dosage", and is intended to refer to the quantity of pharmaceutically active ingredient administered to the individual in need thereof capable of producing the desired therapeutic effect. The term may refer to a single one time dose, in a physically discrete unit, such as, for example, in a pill or injection or may refer to multiple doses in physically discrete units. Alternatively, an effective amount of the pharmaceutically active ingredient may be administered to the individual as, for example, a vaginal cream or pessary or via a dermal patch. The term "effective amount" also encompasses the quantity of pharmaceutically active ingredient administered to the individual, expressed as the number of molecules, moles, grams, or volume per unit body mass of the individual, such as, for example, mol/kg, mg/kg, ng/kg, ml/kg, or the like, sometimes referred to as concentration administered. The effective amount of pharmaceutically active ingredient may vary among individuals and may fluctuate within an individual over time, depending on factors such as, but not limited to, the condition being treated, genetic profile, metabolic rate, biotransformation capacity, frequency of administration, formulation administered, elimination rate, and rate and/or degree of absorption from the route/site of administration.

Implantation failure is a major impediment to early pregnancy progression. Morphological and molecular features of implantation in the mouse and human uterus include formation of apical uterine cell protrusions called the uterodomes (pinopodes), temporary loss of expression of the anti-implantation mucin MUC1, and the induction of phosphorylation of NFkB and STAT3 in the uterine epithelium at the window of implantation.

Experiments were performed demonstrating that aberrant expression of IFN-γ resulted in non-receptive uterine changes. These experiments were performed in the well-established model of human type 1 diabetes, the Non-Obese Diabetic (NOD) mice. Uteri of diabetic NOD mice naturally mated and having undergone artificially stimulated decidualization were compared for implantation defects at 4.5 and 6.5 days post-coitum. Morphologically, uteri of diabetic NOD mice manifested higher rates of peri- and post-implantation embryo loss and exhibited defective maturation of uterine uterodomes at implantation sites. Uterine IFN-γ and MUC1 were aberrantly induced both at the mRNA and protein levels whereas LIF protein expression and the phosphorylation of NFkBp65 and STAT3 were greatly reduced at nidation and during decidualization in the diabetic NOD mice. Thus, as demonstrated by these experiments, aberrant expression of IFN-γ plays a role in mediating non-receptive uterine changes in hyperglycemic NOD mice.

The ability of the pharmaceutically active ingredient tacrolimus to restore normal pregnancy pattern and prevent IUGR was demonstrated in NOD mice. In these studies, pregnancy progression and the glycemic control of mice treated with tacrolimus were examined. In an initial set of experiments, a loading dose of 10 mg/kg was initially administered to mice at the pre-diabetic stage followed by a maintenance dose of 1 or 0.1 mg/kg every other day (q2d) for three weeks after the last injection of which animals were allowed to mate and get pregnant. In an additional set of experiments mice were injected every other day with either 1 or 0.1 mg/kg dose for three weeks during the pre-diabetic stage and after the last injection of which mice were mated and examined for the progress of their pregnancy.

Ultrasonic, vascular resistance index measurements, morphologic analyses were conducted on immunosuppressed and control NOD dams and their gestational uterine samples throughout pregnancy. Uterine, decidual and placental IFN-γ mRNA levels were also measured. Immunosuppressed NOD mice achieved and maintained normal glucose homeostasis with normal pregnancy pattern and a higher rate of viably implanted embryos and fetuses having normal phenotypic appearance. Placentae of NOD mice treated with tacrolimus were more deciduomatous, and the integrity of the stem, anchoring and branching placental villi were maintained. A normal pattern of intra-uterine fetal growth was restored, and importantly, a normal pattern of uterine artery blood flow was achieved and maintained throughout pregnancy in immunosuppressed mice. Lower normal levels of decidual/placental IFN-γ mRNA were detected throughout mid- to late pregnancy in immunosuppressed mice.

Accordingly, as shown by these studies, selective inhibition of IFN-γ production in NOD mice provided an effective therapeutic approach in treating pregnancy failure and IUGR occurrence in autoimmune diabetes.

Additional experiments were conducted in NOD as well as a New Zealand obese (NZO) mouse which shares a common ancestry with the NZB model of systemic autoimmune disease (Bielschowsky, M. & Bielschowsky, F. (1956), Aust. J. exp. Biol. 34:181-198), Lenc and colleagues (Lenc et al (1979) Nature 279: 334-336) and serves as a model of obesity mediated type 2 diabetes and the C57BL6 mouse induced to obesity by diet, referred to as the diet-induced obesity (DIO) model. DIO mice also serve as a model for type II diabetes and polycystic ovarian syndrome (PCOS).

Figure 3A:
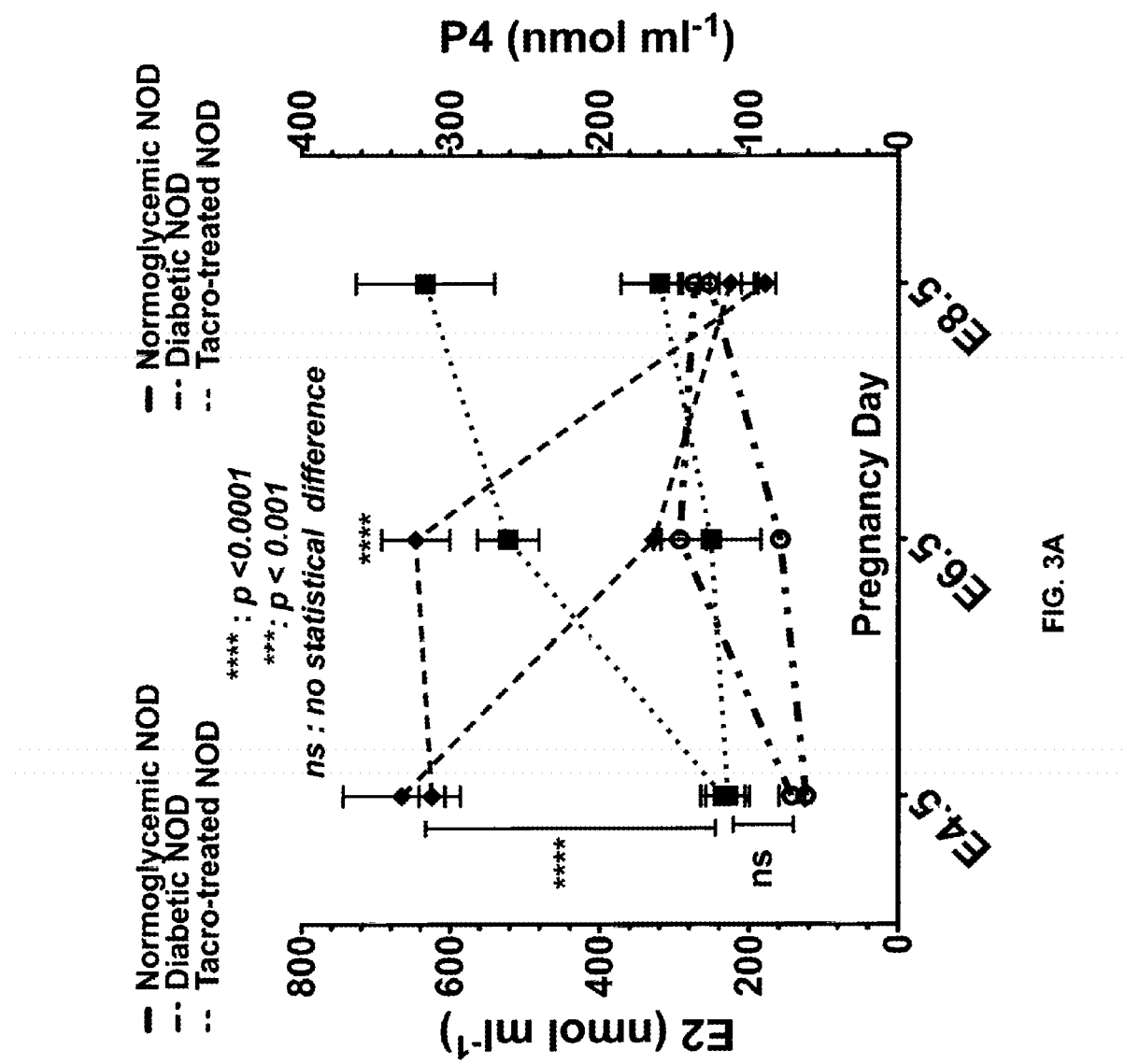
FIGS. 3A through 3C show results of short-term administration of tacrolimus preventing post-ovulation ovarian failure as evident from the normalized secretion of estrogen and progesterone (FIG. 3A), supporting ovarian follicular growth, maturation, ovulation and post-ovulation ovarian functions as measured by increased numbers of secondary follicles (FIG. 3B: S), antral follicles (FIG. 3B: A) and corpora lutea (FIG. 3B: CL) and reducing numbers of atretic follicles (FIG. 3B: AT) and restoring a normal pattern uterine sensitivity to ovarian steroids (as measured by uterine weight ratio during the proliferative and early secretory phases of the estrous cycle) (FIG. 3C) in ovaries of treated diabetic and obese mice.
Figure 3B:
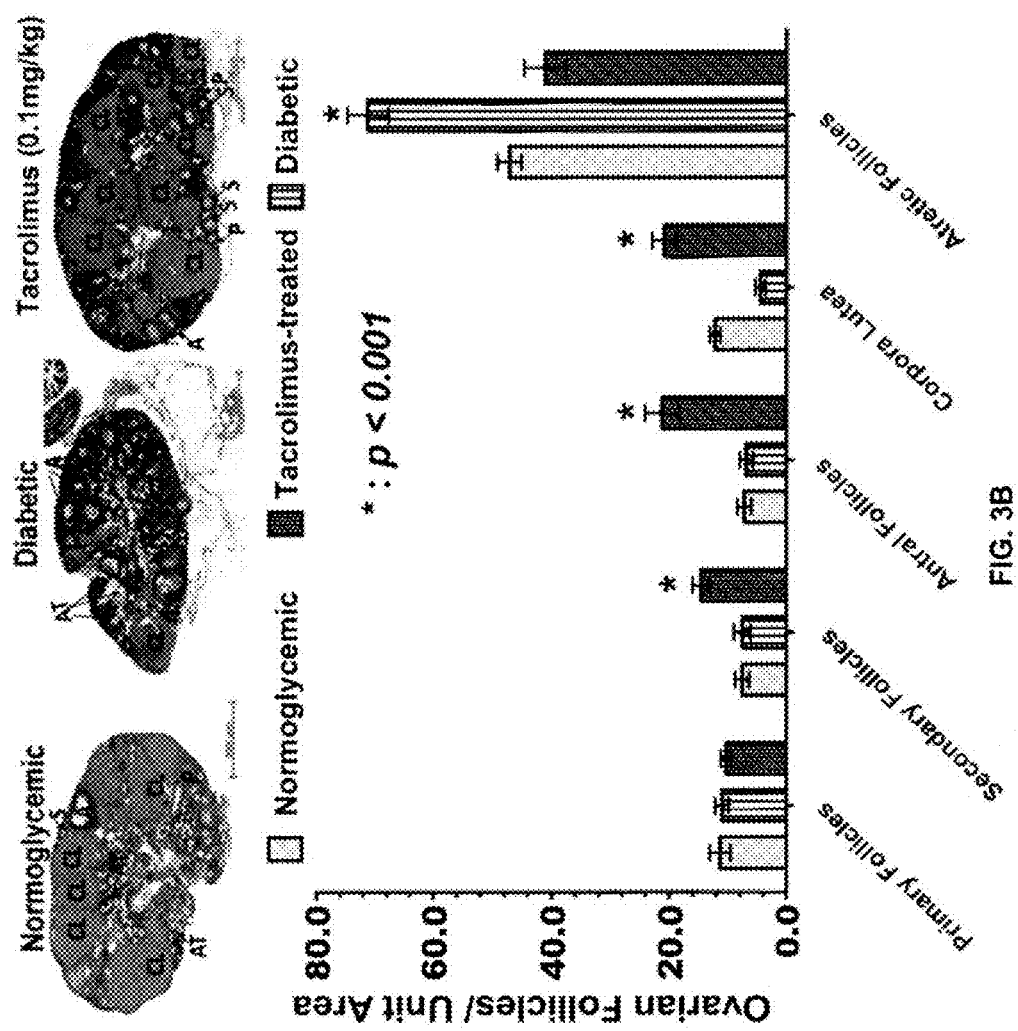
Figure 3C:
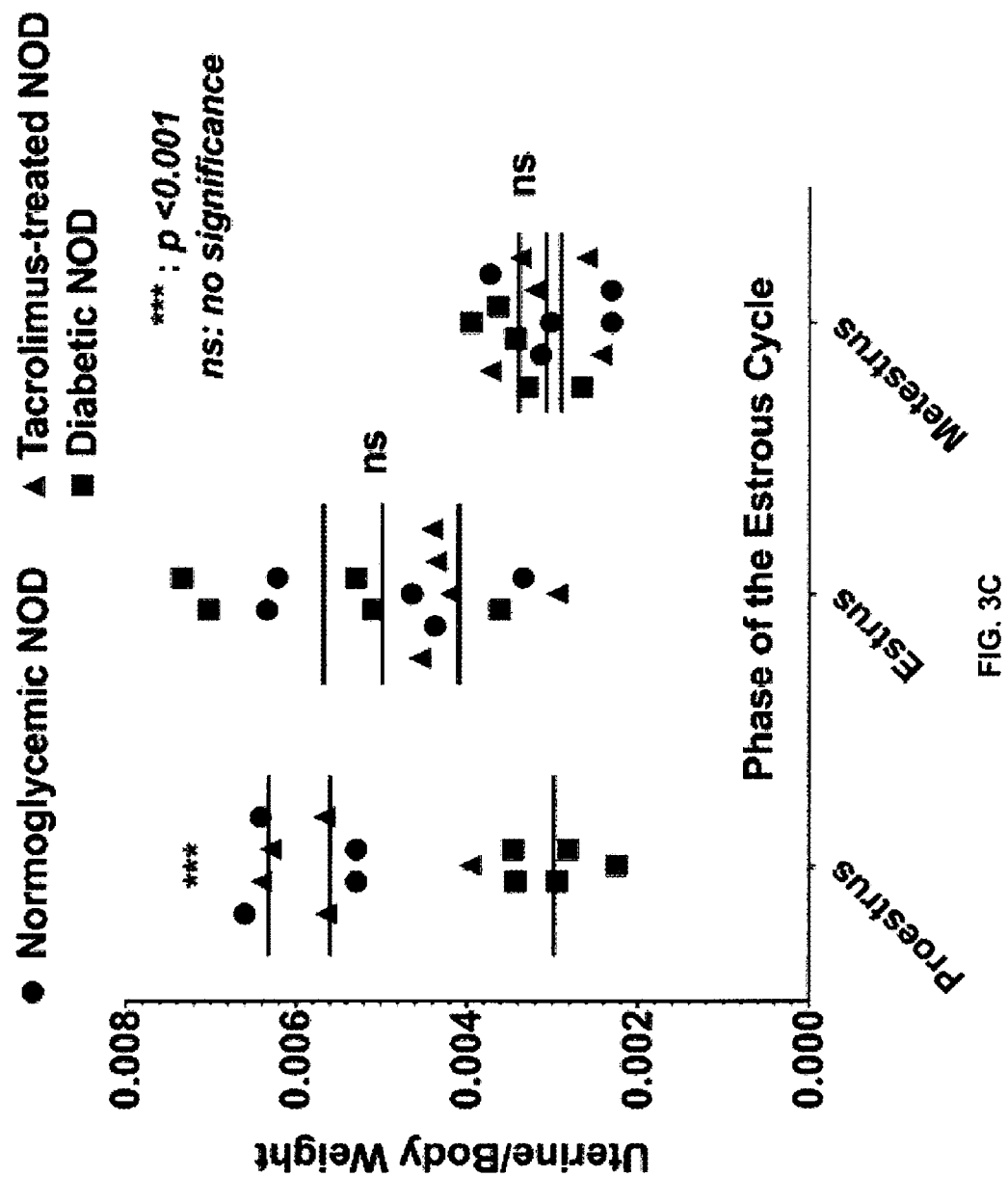

In these experiments, tacrolimus enhanced ovulation, normalized ovarian secretion of estrogen and progesterone and prevented premature luteolysis and post-ovulation ovarian failure thereby preventing development of PCOS-like phenotype in treated mice. As shown in FIG. 3, tacrolimus enhanced ovarian function and prevented post-ovulation and post-embryo implantation ovarian failure, both of which are major hurdles to the success of implantation in women candidates for IVF. Implantation success rates among the tacrolimus-treated NOD, NZO and DIO mice were accompanied by the restoration of a normalized ovarian secretion of Progesterone (P4) and Estrogen (Estradiol: E2) during peri- and post-implantation period in all mated, treated mice. High rates of peri- and post-implantation failure in the vehicle treated diabetic mice were associated with failure of the ovaries to support early pregnancy as manifested by the disappearance and resolution of the corpora lutea (CL) from ovaries of diabetic and obese mice at peri- and post-implantation periods. The short-term of administration of tacrolimus prevented post-ovulation ovarian failure as evident from the normalized secretion of estrogen and progesterone (FIG. 3A), supported ovarian follicular growth, maturation, ovulation and post-ovulation ovarian functions as measured by increased numbers of secondary follicles (FIG. 3B: S), antral follicles (FIG. 3B: A) and corpora lutea (FIG. 3B: CL) and reduced numbers of atretic follicles (FIG. 3B: AT) and the restoration of a normal pattern uterine sensitivity to ovarian steroids (as measured by uterine weight ratio during the proliferative and early secretory phases of the estrous cycle; FIG. 3C). As shown in FIG. 3C, a significant improvement in uterine growth was achieved in the tacrolimus-treated mice during the early proliferative phase of their estrous cycle represented by the proestrus stage suggesting increased uterine responsiveness to ovarian steroids in the tacrolimus-treated diabetic mice. Uterine weight change is a sensitive parameter for assessing uterine response to ovarian steroids. In preparation for successful implantation, the administration of tacrolimus restored normal uterine growth pattern in the vast majority of treated mice. FIG. 3C is a representative group scattered graph depicting uterine mass corrected to animal body weight in tacrolimus-treated versus vehicle-treated and their normoglycemic control mice prior to mating and during selected phases of the estrous cycle in these animals. The uteri of diabetic and obese mice demonstrated higher resistance to ovarian steroid thereby impeding the organ response in preparing for embryo implantation.

Figure 3D:
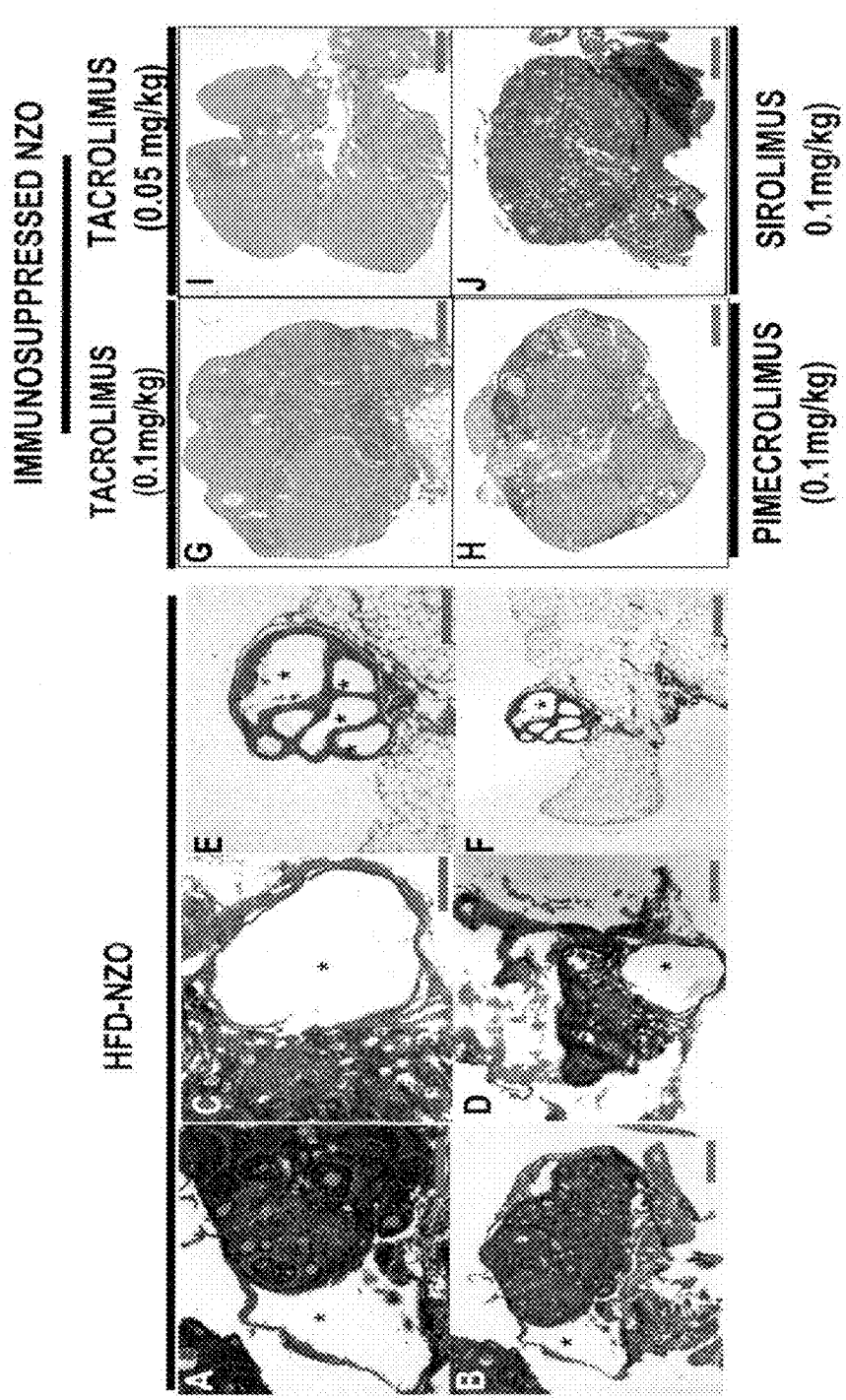
FIG. 3D shows hematoxylen- and eosin-stained thin sections of ovaries from macrolide-treated chronically high fat fed female NZO mice. Macrolide treatment restored ovarian morphology and inhibited the development of ovarian cysts in these treated mice. Despite some individual differences in their therapeutic efficacy, all tested macrolides significantly inhibited ovarian follicular atresia (p<0.01) and cyst formation (p<0.001) (compare A-F with G-J and corresponding bar graphs), and restored follicular growth pattern in the ovaries of the treated mice. Statistical differences between groups were measured by two-way analysis of variance (ANOVA) followed by Bonferroni post-hock t-test comparing effect of all tested macrolides on mean follicular structure counts/unit area at 95% confidence. Scale bars=200 μm for B, D, F, G, H, I, J and 50 μm for A, C, E. N=10 (HFD-NZO), 6 per treatment group. A, C and E are higher magnifications of B, D and F respectively. * denoting ovarian cyst(s).

Macrolide treatment restored ovarian morphology and inhibited the development of ovarian cysts in chronically high fat diet fed NZO mice treated with tacrolimus, pimecrolimus and sirolimus, as shown in FIG. 3D. Despite some individual differences in their therapeutic efficacy, all tested macrolides significantly inhibited ovarian follicular atresia ($p<0.01$) and cyst formation ($p<0.001$) (compare A-F with G-J and corresponding bar graphs), and restored follicular growth pattern in the ovaries of the treated mice. (This suggests that inhibiting IFNγ and/or IL2 signaling may assist inhibition of ovarian cyst formation, e.g., in infertile subjects, such as, for example, PCOS subjects.)

Figure 4A:
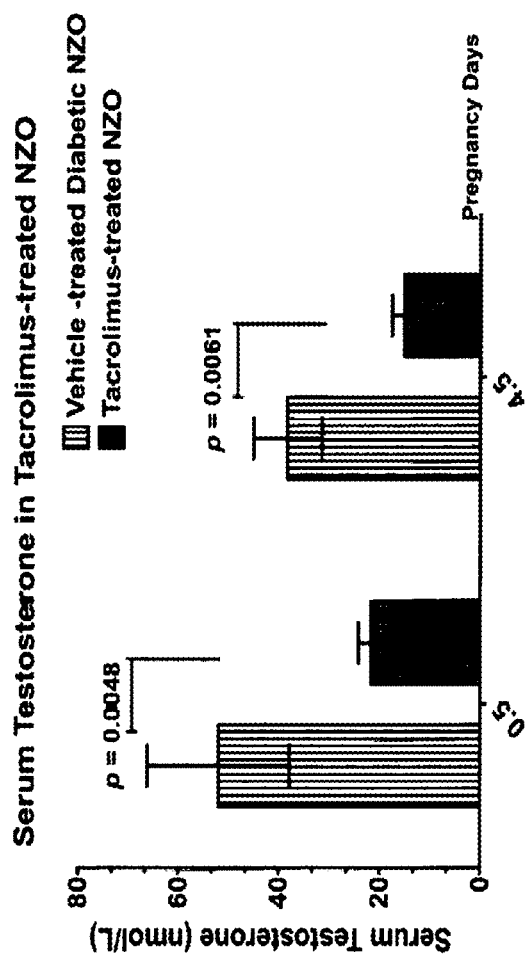
FIGS. 4A and 4B show results of short-term administration of tacrolimus preventing the development of Polycystic Ovary (PCOS) phenotype in all treated type2 diabetic and obese mice as determined by hypertestosteronism (hyperandrogenism.
Figure 4B:
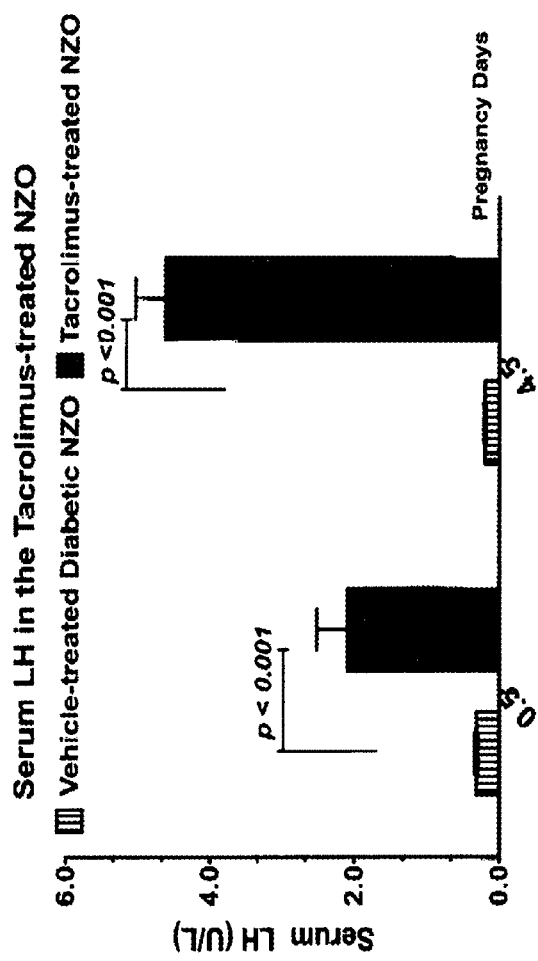

As further shown in FIG. 4, tacrolimus prevented the development of PCOS phenotype in all treated type 2 diabetic and obese mice. Hypertestosteronism (Hyperandrogenism) and low serum levels of Luteinizing hormone (LH) are among the cardinal biochemical features of established PCOS syndrome. This demonstrated efficacy of tacrolimus in preventing PCOS development in mice fed with a high fat diet correlates with improved fertility and energy expenditure in all treated type 2 diabetic and obese mice. Serum samples from tacrolimus-treated and saline-injected type 2 diabetic NZO and DIO mice were analyzed for their testosterone and luteinizing hormone (LH) levels in the morning of vaginal plug detection after mating and at 4.5 days later to assess the integrity of their pituitary-ovarian endocrine interactions during successful mating and at embryo implantation. Tacrolimus restored normal pituitary-ovarian response and hormonal release to mating in all treated type 2 diabetic and obese mice. These results support a pathological role of aberrant IFN-γ production in these mice on ovarian functions and pituitary-ovarian interactions during normal mating. These results further support the use of tacrolimus in treating hypertestosteronism or hyperandrogenism.

Figure 5A:
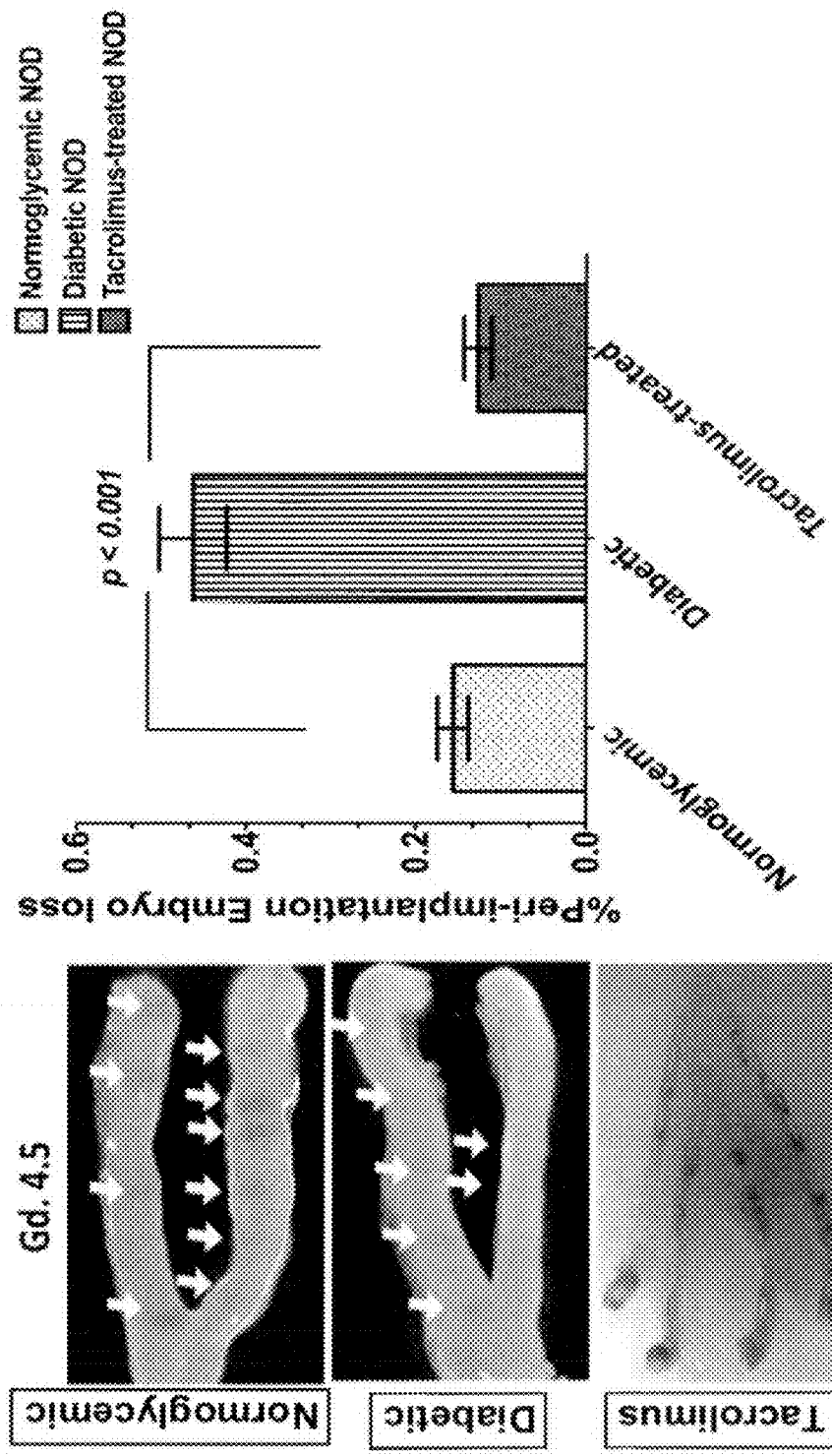
Figure 5B:
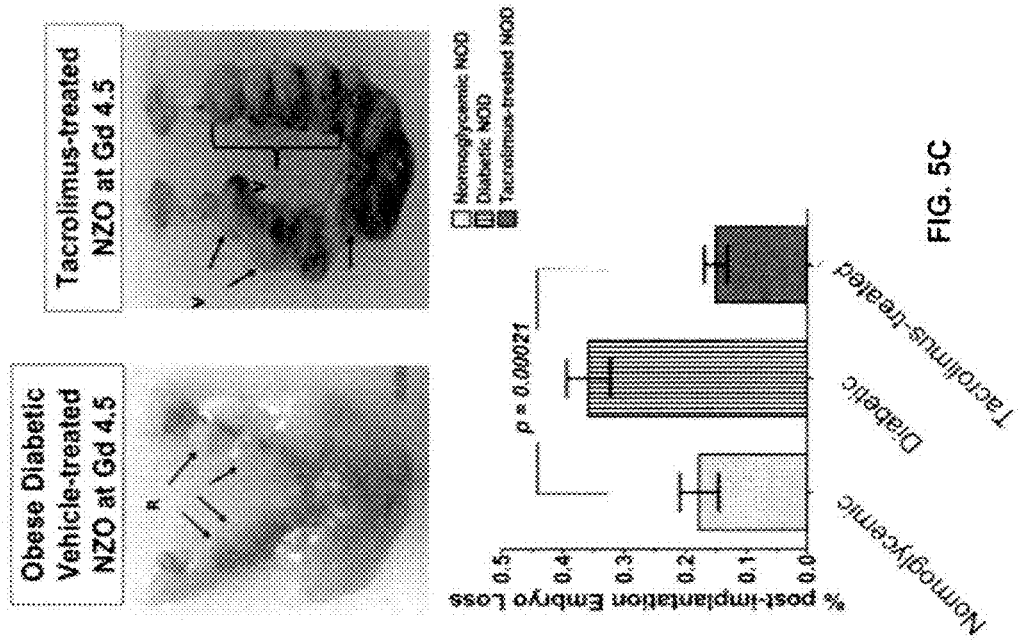
Figure 5C:
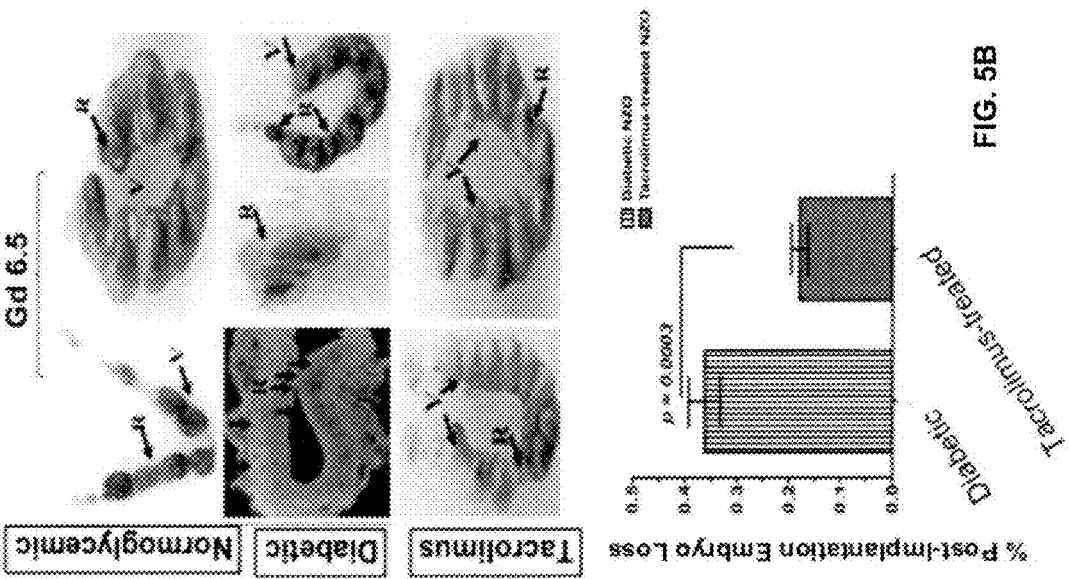

Tacrolimus enhanced implantation rate and supported post-implantation embryo development in treated diabetic and obese mice. As shown in FIGS. 5 and 6A, the short-term administration of tacrolimus enhanced implantation rate (compare photomicrographs in FIG. 5A and their corresponding graph bars) and supported post-implantation embryo development, promoted early pregnancy progression and reduced rates of embryonic and fetal resorption in all treated mated mice (compare photomicrographs in FIG. 5B and their corresponding graph bars and FIG. 6B) and maintained high live birth rates of normal pups. The photomicrographs in FIG. 5 are representative of implantation sites obtained during pregnancy days 4.5 and day 6.5 from tacrolimus treated NOD (FIG. 5A and FIG. 5B) and NZO (FIG. 5C and FIG. 5D) mice versus their vehicle treated diabetic and normoglycemic control mice.

Additional experiments showed pimecrolimus (0.1 mg/kg) and sirolimus (0.1 mg/kg) administered subcutaneously every other day for three weeks significantly improved implantation rate (p<0.05) compared to vehicle-treated control female mice, as well. See FIGS. 6A and 6B. The same treatments also significantly reduced the embryonic and fetal absorption rate compared to vehicle-treated controls (p<0.05).

While all of the tested macrolides were effective at enhancing fertility, tacrolimus had unexpectedly greater comparative effects.

Figures 7A, 7B, 7C:
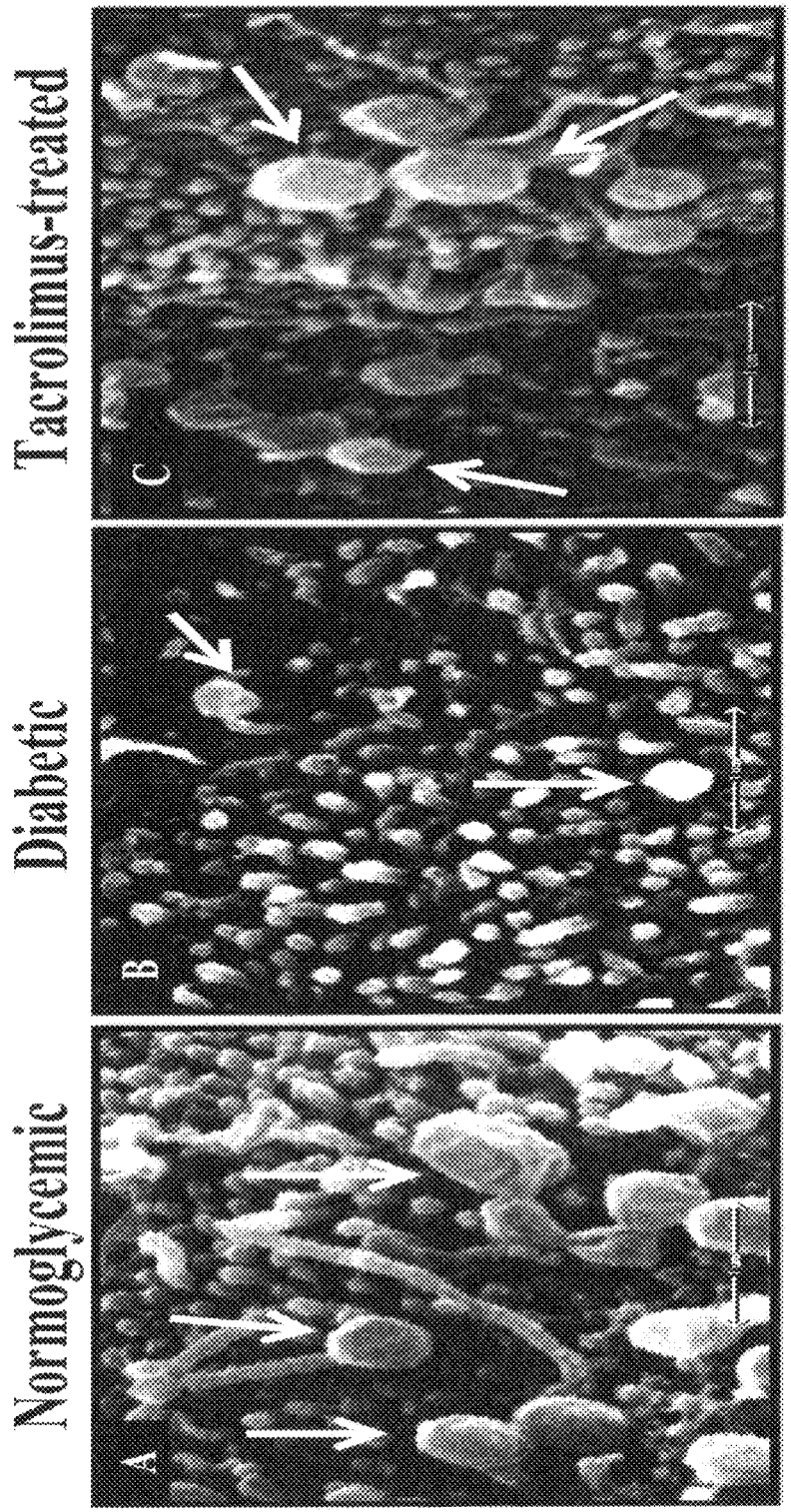
FIGS. 7A through 7F show results of short term administration of tacrolimus correcting implantation defects in the uteri of treated diabetic and obese mice during embryo implantation. Implantation defects in the diabetic mice consisted of failure of uterodome formation (white arrows in FIGS. 7A-7C), deficient production of the major implantation cytokine LIF during embryo implantation (compare normoglycemic in lanes 1-2 with the diabetic in lane 3-4 and those tacrolimus treated in lanes 5-6 of FIG. 7D), and aberrant overproduction of embryotoxic pro-inflammatory cytokines, namely IFN-γ, TNFα and IL16 (FIG. 7E) and those involved in materno-fetal rejection, namely the Interleukin 12 family (FIG. 7F) in the uteri of diabetic mice during embryo implantation. Scale bars=1 μm in FIGS. 7A-7C. n=7-10. Samples in the lanes of FIG. 7D are: 1: Normoglycemic at E4.5, 2: Normoglycemic at E6.5, 3: Diabetic at E4.5, 4: Diabetic at E6.5, 5: Tacrolimus-treated at E4.5 and 6: Tacrolimus-treated at E6.5.
Figure 7D:
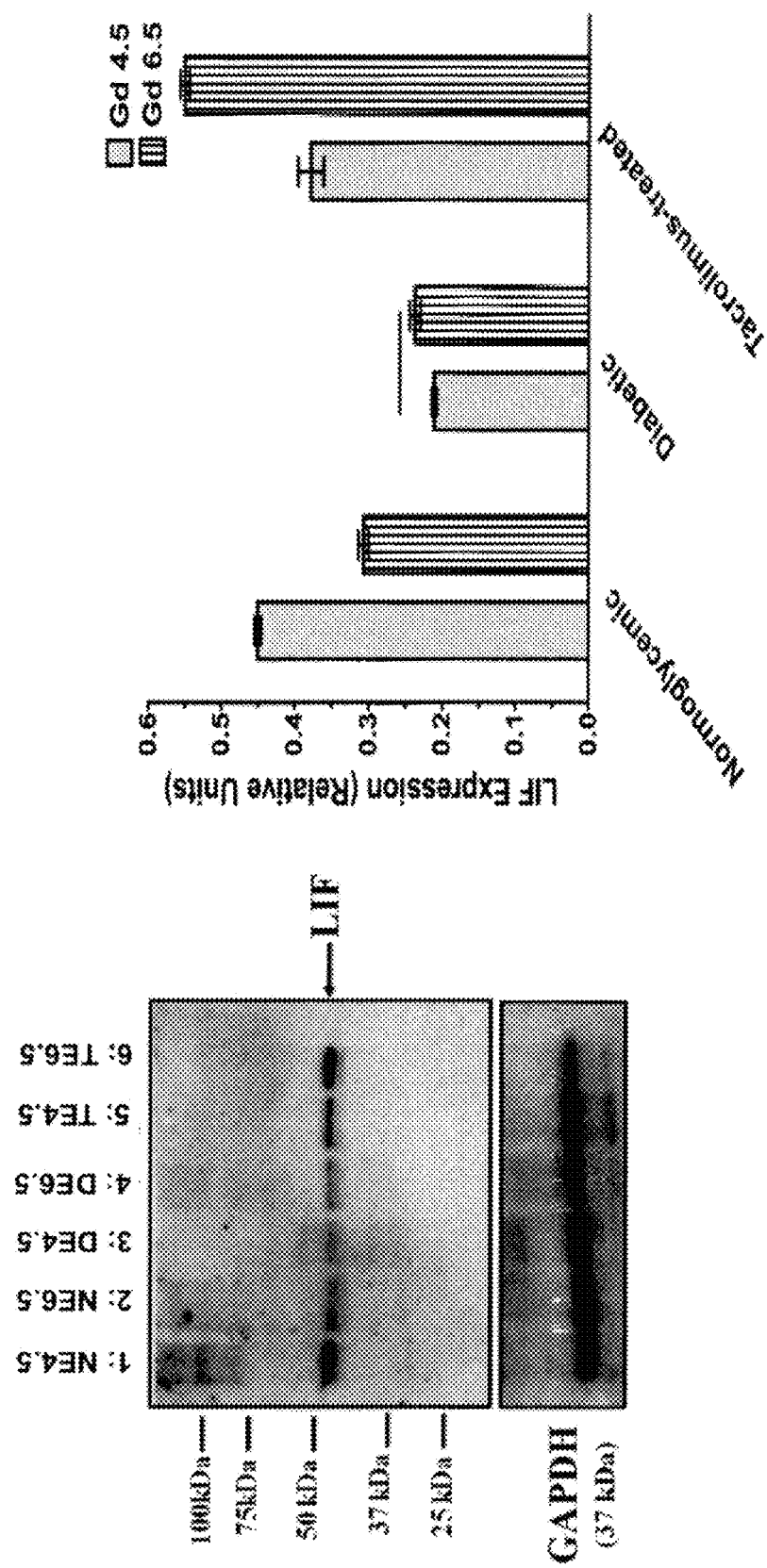

Tacrolimus also corrected implantation defects in the uteri of treated diabetic and obese mice during embryo implantation. Implantation defects in the diabetic mice consisted of failure of uterodomes formation, deficient production of the major implantation cytokine LIF during embryo implantation and aberrant overproduction of embryotoxic pro-inflammatory cytokines, namely IFN-γ, TNFα and IL16 and Interleukin 12 family in the uteri of diabetic mice during embryo implantation. As shown in FIG. 7, implantation defects in the diabetic NOD mice consisted of failure of uterodomes formation (white arrows in FIGS. 7A-7C), deficient LIF production during embryo implantation (compare normoglycemic in lanes 1-2 with the diabetic in lane 3-4 and tacrolimus-treated in lanes 5-6 of FIG. 7D), and aberrant overproduction of embryotoxic pro-inflammatory cytokines, namely IFN-γ, TNFα and IL16 (FIG. 7E) and those involved in materno-fetal rejection, namely the Interleukin 12 family (FIG. 7F) in the uteri of diabetic mice during embryo implantation. FIGS. 7A-C are representative scanning electron photomicrographs of the uterine luminal surface in normoglycemic (FIG. 7A), vehicle-treated diabetic (FIG. 7B) and those tacrolimus-treated (FIG. 7C) NOD mice providing evidence for the efficacy of tacrolimus in inducing maturation of uterodomes (arrows) at implantation sites during pregnancy day 4.5 in all treated mice. Uterodomes are apical uterine epithelial cell membrane protrusions that are typically devoid of the majority of cell membrane glycoprotein barriers to embryo implantation such as MUC1. Failure of timely embryo implantation in the vehicle-treated diabetic mice is immunologically mediated and is characteristically associated with failure of uterodome maturation (see the relative abundance of immature uterodomes lacking the swollen tips in FIGS. 7A and 7C). FIG. 7D shows a representative Western blot of detection of Leukemia Inhibitory Factor (LIF), an essential cytokine biomarker of successful implantation, in the uteri of tacrolimus-treated versus vehicle-treated and the normoglycemic control mice. Consistent with the successful induction of implantation and proper uterodome maturation in the tacrolimus-treated mice, intensity level of the detected LIF chemiluminescent signals (lanes 5-6) indicate that tacrolimus-induced LIF protein expression in the uteri of treated diabetic mice during the time of embryo implantation that coincides with day 4.5 postcoitum. Tacrolimus-induced LIF expression extends into day 6.5 postcoitum indicative of successful post-implantation embryo development. Deficient LIF expression and uterodome maturation failure are both immunologically mediated and cannot be corrected with the use of conventional hormonal therapy such as the use of gonadotropin preparations in diabetic subjects.

Figure 7E:
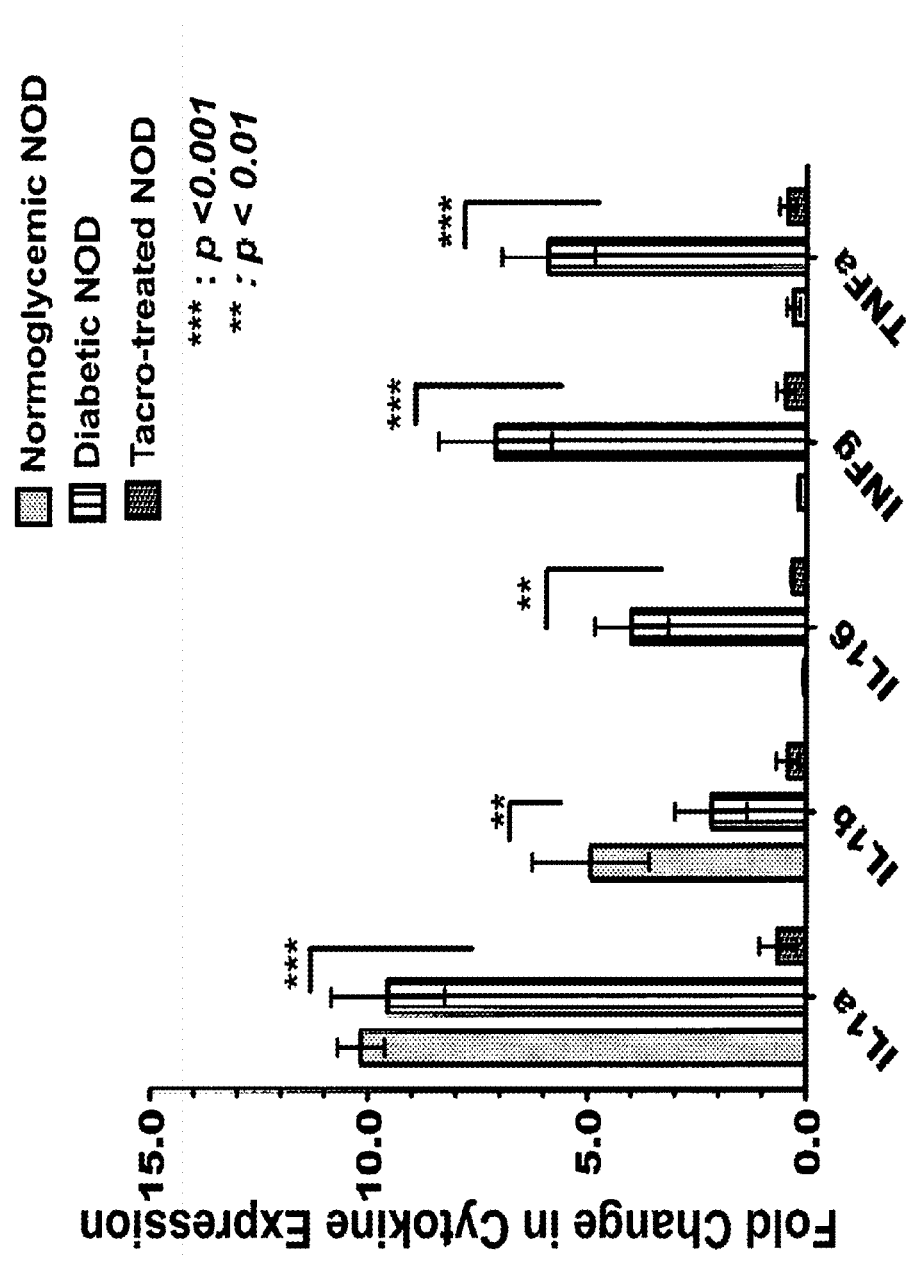
Figure 7F:
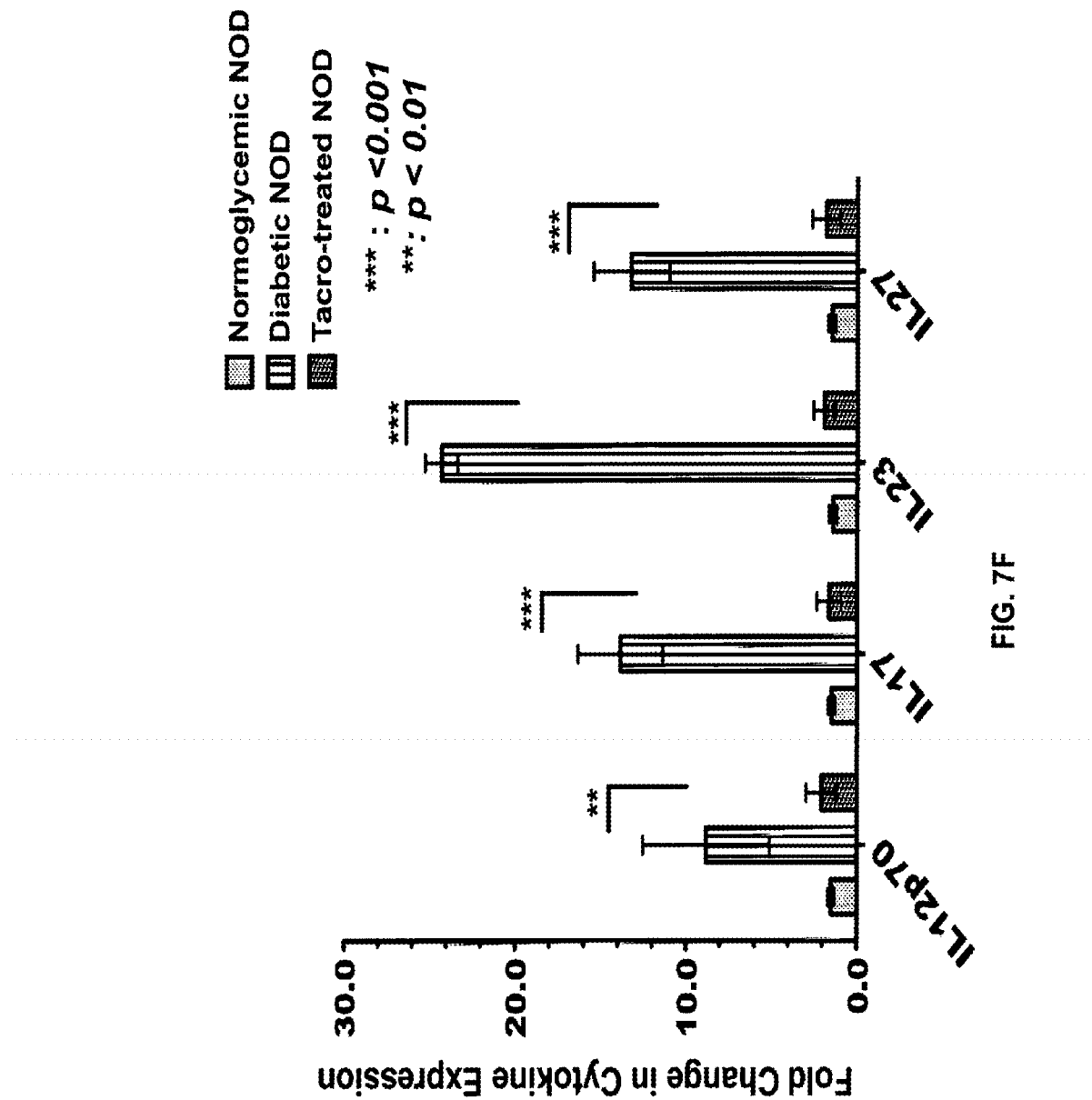

Cytokine multiplex profiling in the uteri of tacrolimus-treated diabetic NOD mice at peri-implantation showed a transient local uterine inflammatory (Th1-biased) response driven by the over-expression of IFN-γ resulted in pathological induction of TNFα and IL16 whereas no significant effect was observed on Interleukin 1 alpha (IL-1a) and IL-1beta (IL-1b) and IL12 family namely IL12p70, IL17, IL23 and IL27 in diabetic mice (see FIG. 7E). In all untreated or vehicle-treated diabetic mice, an aberrant over-expression of IFN-γ, TNFα and IL16 accounted for the immune-cytotoxicity related implantation failure in these mice. The short-term administration of tacrolimus prior to mating resulted in significant inhibition of the vast majority of Th1-induced cytokines, notably IFN-γ, IL16, TNFα and IL12 family cytokines which are reportedly involved in mediating IFN-γ-cytotoxicities such as aberrant stimulation of auto-antibodies and the release of tissue-factor laden microparticles by aberrantly activated monocytes and macrophages. The ability of short-term treatment with tacrolimus in downregulating members of IL12 family cytokines, as depicted in FIG. 7F, at the time of implantation may explain the high viability of implanted embryos in all treated mice.

Figure 8:
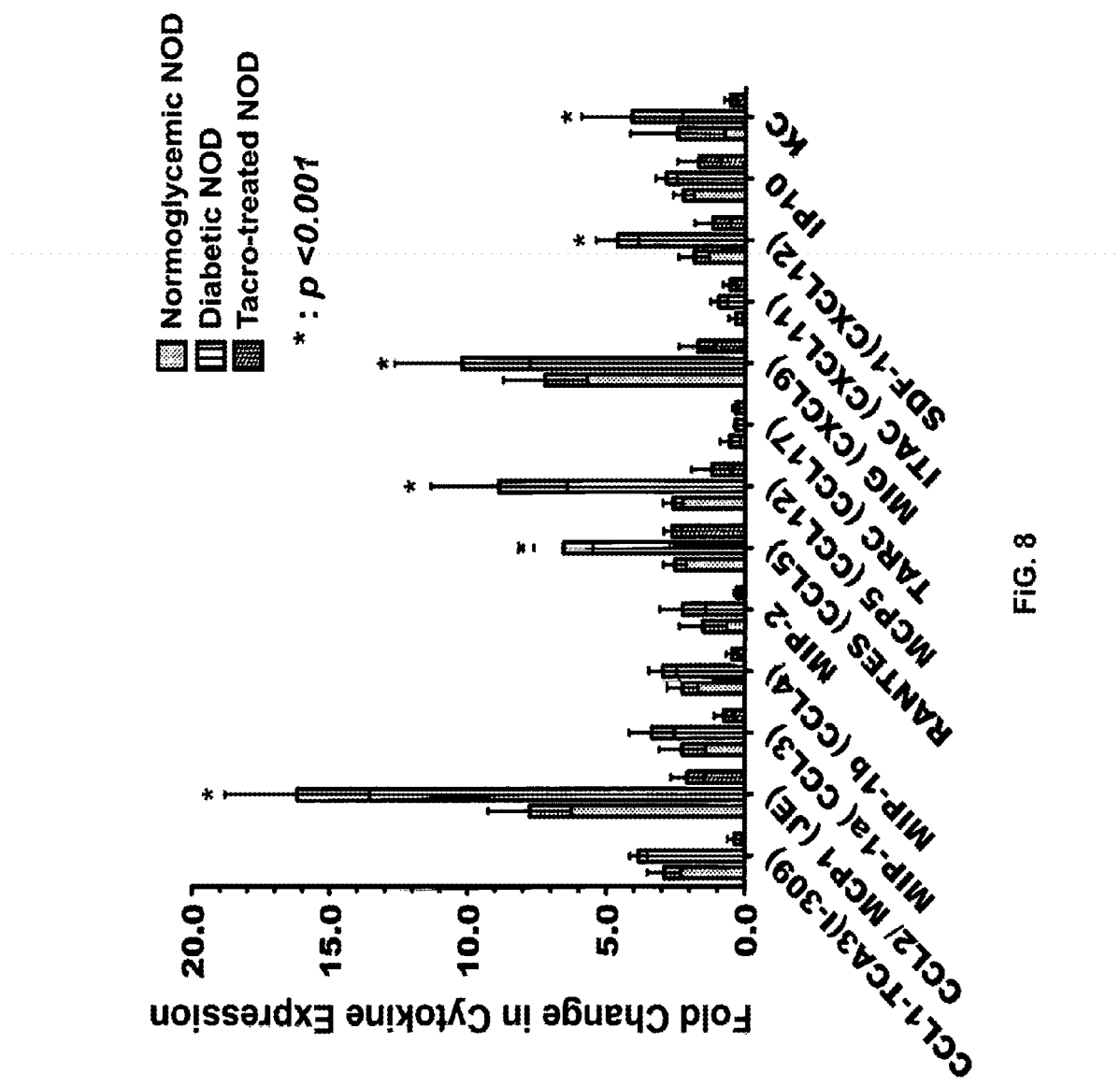
FIG. 8 shows results of short-term administration of tacrolimus to diabetic mice prior to mating significantly downregulating the uterine expression of cytokines involved in inflammation, T-cell cytotoxicity and blood coagulation at the peri-implantation period including six major IFN-γ-regulated inflammatory cytokines involved in T-cell mediated cytotoxicity and platelet adhesiveness.

As shown in FIG. 8, this tacrolimus dosing regimen resulted in pan-inhibition of cytokines involved in inflammation, T-cell cytotoxicity and blood coagulation at the peri-implantation period, most of which are IFN-γ regulated. Thus tacrolimus may also provide benefit to that class of women that have recurrent miscarriages due to a prothrombotic state.

Figure 9:
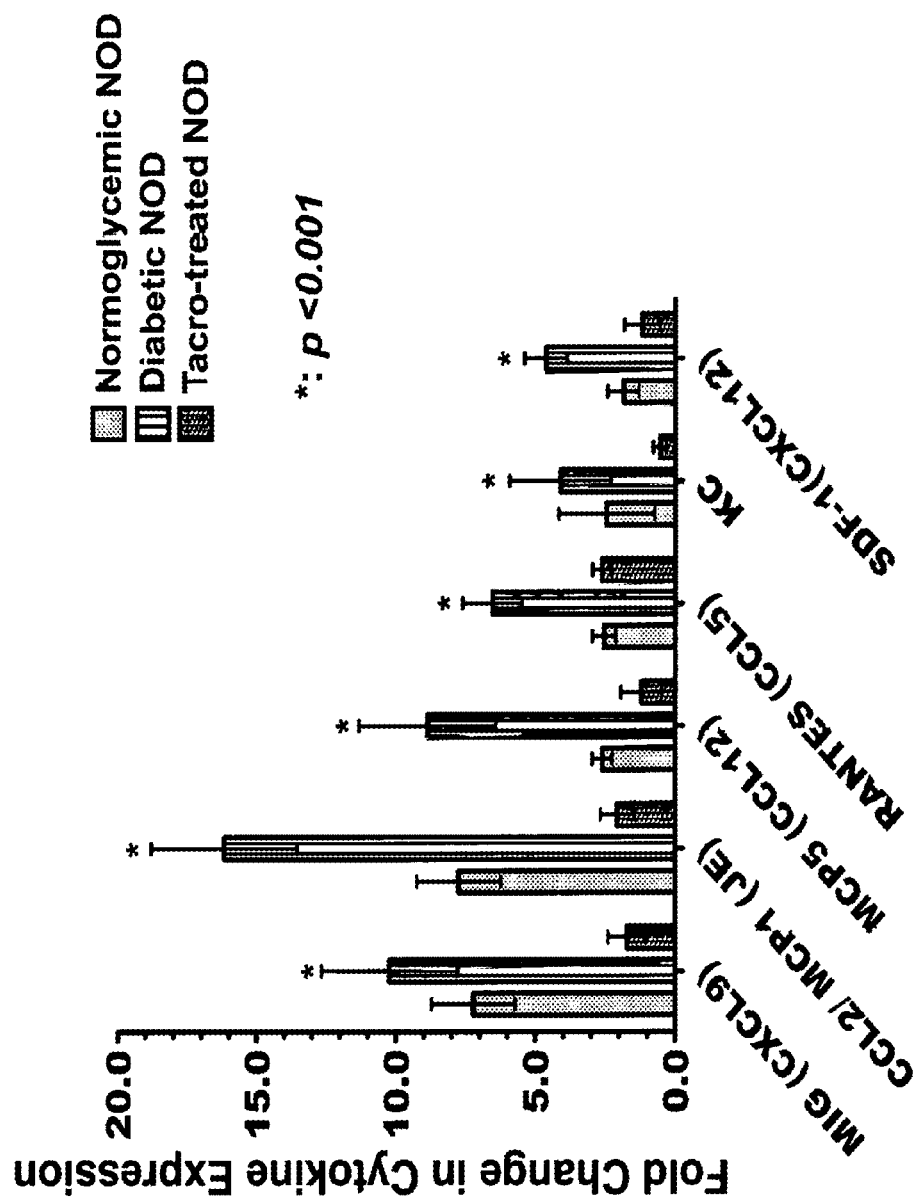
FIG. 9 shows results of short-term administration of tacrolimus to diabetic mice prior to mating significantly downregulating the uterine expression of six major IFN-γ-regulated inflammatory cytokines involved in T-cell mediated cytotoxicity and platelet adhesiveness at the peri-implantation period, these cytokines namely are: Macrophage/Monocyte Chemoattractant Protein-1 (MCP1; CCL2;JE), Monocyte Chemoattractant protein 5 (MCP5/CCL12), Monokine induced by IFN-γ (Mig; CXC chemokine ligand 9; MIG9), Regulated on Activation Normal T Cell Expressed and Secreted (RANTES), Stromal cell-derived factor-1 (SDF-1), and the TNFα-regulated Monocyte chemoattractant chemokine CXCL1 (KC).
Figure 10:
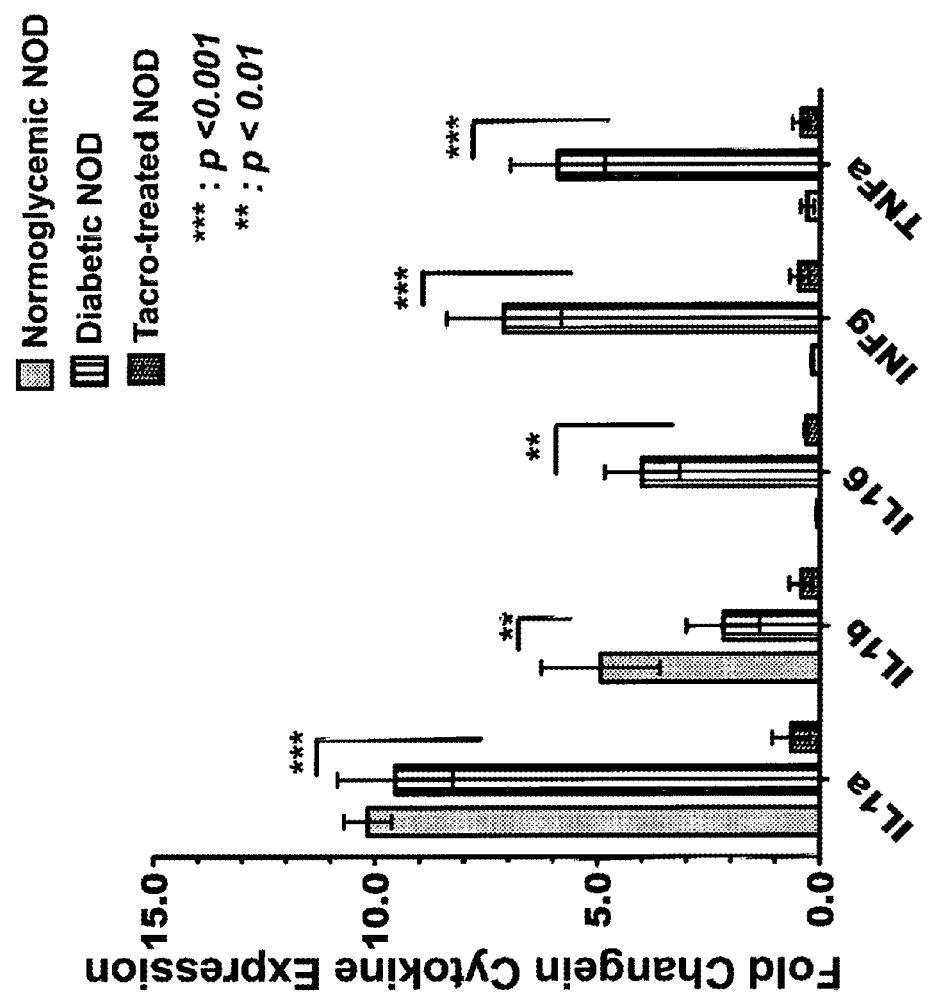
FIG. 10 shows results of short-term administration of tacrolimus prior to mating resulted in significant inhibition of all Th1-induced cytokines, notably, IFN-γ, IL16 and TNFα in the uteri of diabetic mice during peri-implantation. A transient local uterine inflammatory (Th1-biased) response driven by the over-expression of Interleukin1 alpha (IL-1a) and, to a lesser extent that of IL-1beta (IL-1b) accompanies successful implantation in mouse and human. In all untreated or vehicle-treated diabetic mice, an aberrant over-expression of IFN-γ, TNFα and IL16 accounts for the immune-cytotoxicity related implantation failure in these mice.
Figure 11:
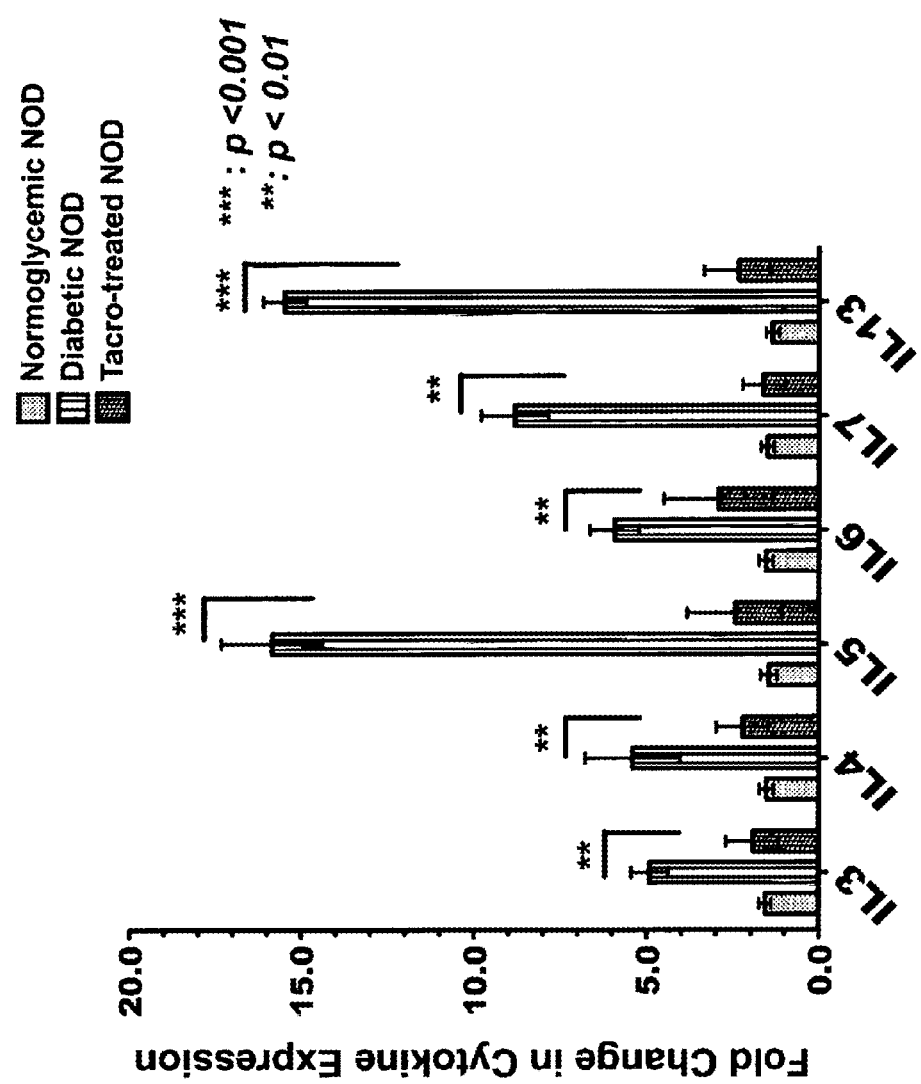
FIG. 11 shows results of short-term administration of tacrolimus to the diabetes prone mice restoring a normalized pattern of the pro-inflammatory cytokines expression in the uteri of treated diabetes prone mice at the time of implantation. Tacrolimus specifically restored normalized level of IL5, IL7 and IL13 expression at the time of implantation thereby eliminating risk of maternal rejection and hypersensitivity to the embryonic presence and promoted post-implantation development.
Figure 12:
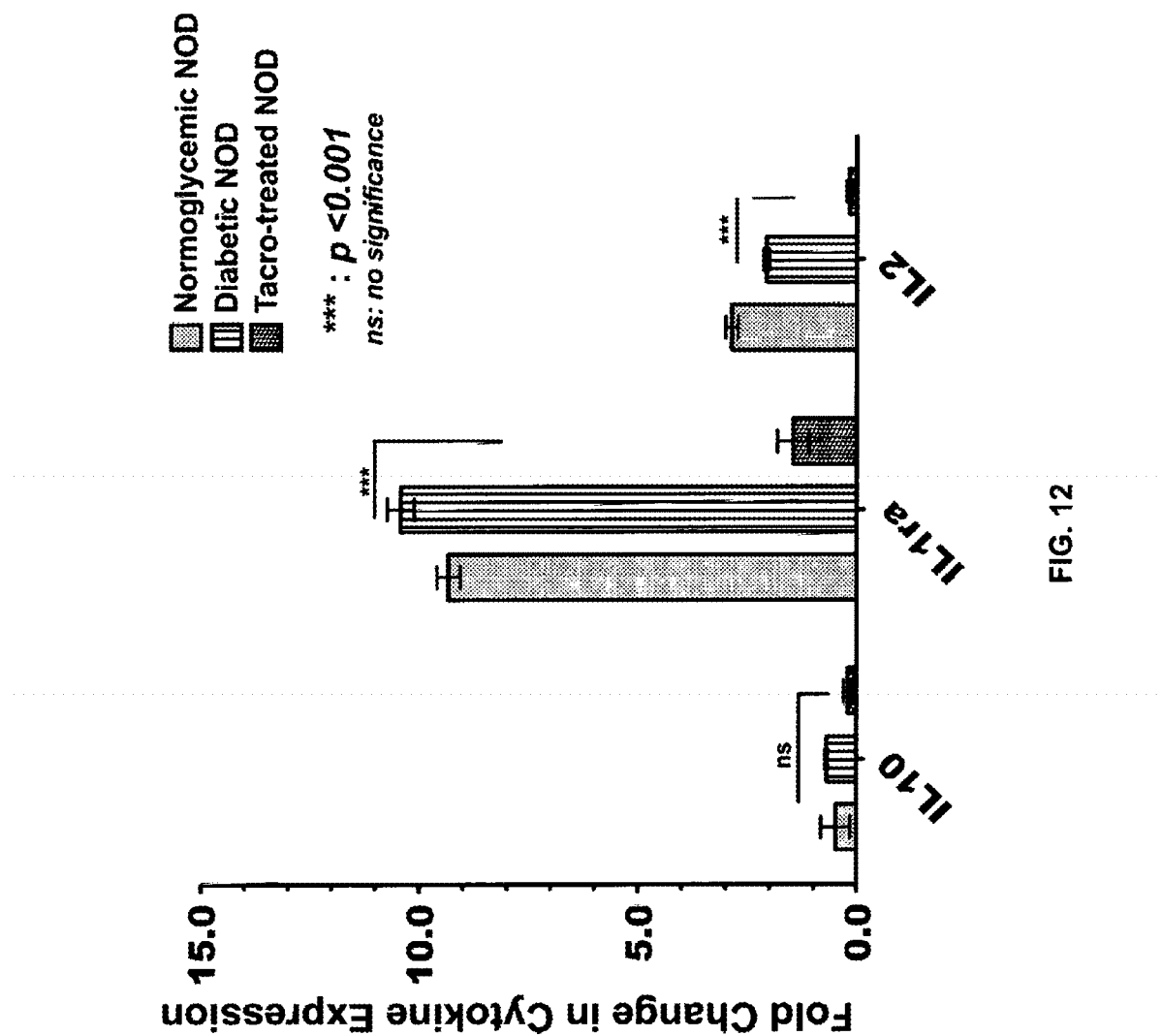
FIG. 12 shows an observed inhibition of some anti-inflammatory cytokines such as IL-1ra, IL10 and IL2 in the tacrolimus-treated diabetes prone mice supportive of the minimal requirement of these cytokines in implantation. The selective manner of the Th2 cytokine inhibition observed with use of tacrolimus in the diabetes prone mice is indicative of the restoration of a beneficial balance in the maternal Th1/Th2 immune response that resulted in a successful peri and post-implantation development, thereby eliminating the need for a concomitant use of an adjuvant therapeutic agent in achieving such an embryo-tolerant uterine milieu at implantation.

As further shown in FIG. 9, short-term administration of tacrolimus to the diabetic mice prior to mating significantly downregulated the uterine expression of six major IFN-γ-regulated inflammatory cytokines involved in T-cell mediated cytotoxicity and platelet adhesiveness at the peri-implantation period, these cytokines namely are: Macrophage/Monocyte Chemoattractant Protein-1 (MCP1; CCL2;JE), Monocyte Chemoattractant protein 5 (MCP5/CCL12), Monokine induced by IFN-γ (Mig; CXC chemokine ligand 9; MIG9), Regulated on Activation Normal T Cell Expressed and Secreted (RANTES), Stromal cell-derived factor-1 (SDF-1), and the TNFα-regulated Monocyte chemoattractant chemokine CXCL1 (KC). However, as shown in FIG. 10, short-term administration of tacrolimus to the diabetes prone mice restored a normalized pattern of the pro-inflammatory cytokines expression in the uteri of treated diabetes prone mice at the time of implantation. Tacrolimus specifically restored normalized levels of IL5, IL7 and IL13 expression at the time of implantation thereby eliminating risk of maternal rejection and hypersensitivity to the embryonic presence and promoted post-implantation development (See FIG. 11). Furthermore, as shown in FIG. 12, the observed inhibition of some anti-inflammatory cytokines such as IL-1ra, IL10 and IL2 in the tacrolimus-treated diabetes prone mice is indicative of the minimal requirement of these cytokines in implantation. The selective manner of Th2 cytokine inhibition observed in following tacrolimus administration to the diabetes prone mice provides evidence for the restoration of a beneficial balance in the maternal Th1/Th2 immune response that resulted in a successful peri and post-implantation development, thereby eliminating the need for a concomitant use of an adjuvant therapeutic agent in achieving such an embryo-tolerant uterine milieu at implantation.

Tacrolimus reduced the rates of still births and malformations associated with the diabetic gestation and restored normal term pregnancy with high rate of live births in the treated diabetic and obese mice. The successful use of tacrolimus in reducing still birth rates and preventing fetal malformations in the diabetic and obese mice is supportive of the etiological role for IFN-γ in the pathophysiology of fetal loss in diabetes and obese subjects. FIG. 13 provides a comparison between the external morphological features and liver versus still birth rates in near-term (Gd.16.5) pups delivered to tacrolimus-treated NOD (FIG. 13A) versus vehicle-treated diabetic NOD (FIG. 13B) and their normoglycemic control mice (FIG. 13C). FIGS. 13D and 13E show a similar comparison of rates of live births and external morphological features of pups delivered to diabetic NZO and DIO mice at pregnancy day 16.5 (FIG. 13D) versus those age-matched pups delivered to tacrolimus-treated NZO and DIO mice (FIG. 13E). As shown by these experiments, short-term administration of tacrolimus to the obese and diabetic mice proved successful in restoring normal term pregnancy, reducing still birth rates and preventing the development of fetal malformations in the diabetic subjects.

Figures 14A, 14B:
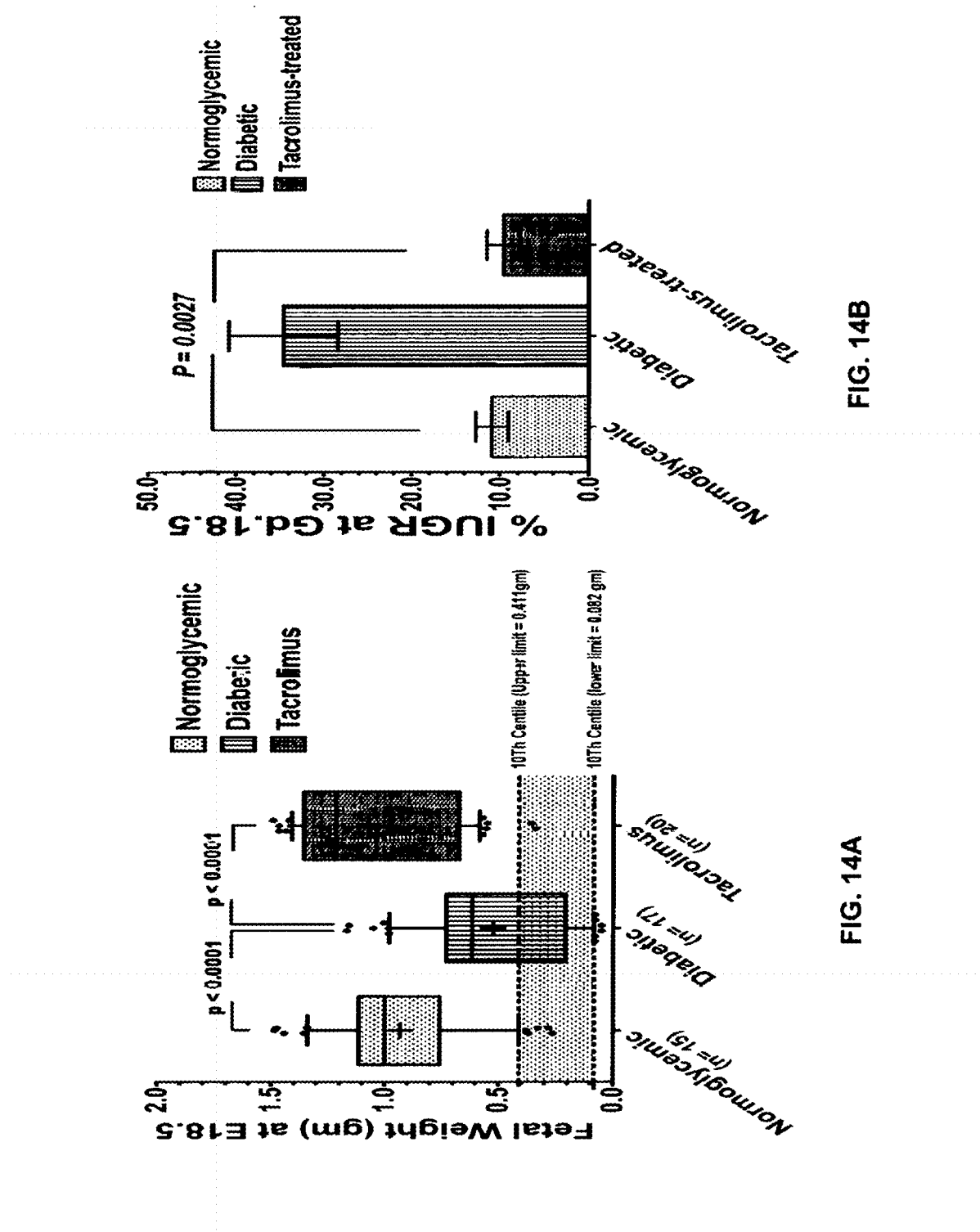
FIGS. 14A and 14B show representative fetal weights (FIG. 14A) and percent of dams with intrauterine growth restricted (IUGR) pups (FIG. 14B) as measured on day 18.5 of pregnancy in the tacrolimus-treated diabetic mice versus vehicle-treated diabetic dams and those normoglycemic control cohorts. Whiskers in FIG. 14A represent the $10^{th}$ and $90^{th}$ percentiles of fetal body weight. Pups with weights below the $10^{th}$ percentile of the normoglycemic control were considered intrauterine growth restricted (IUGR) as indicated by the shaded region. The short-term administration of tacrolimus (0.1 mg/kg subcutaneously every other day between weeks 9-11 of age) significantly improved fetal body weight (FIG. 14A) and inhibited risk of IUGR development in pregnant diabetic mice (FIG. 14B). Numbers in brackets in FIG. 14A represents number of pups examined. "n" denotes number of dams. p<0.05.
Figure 15:
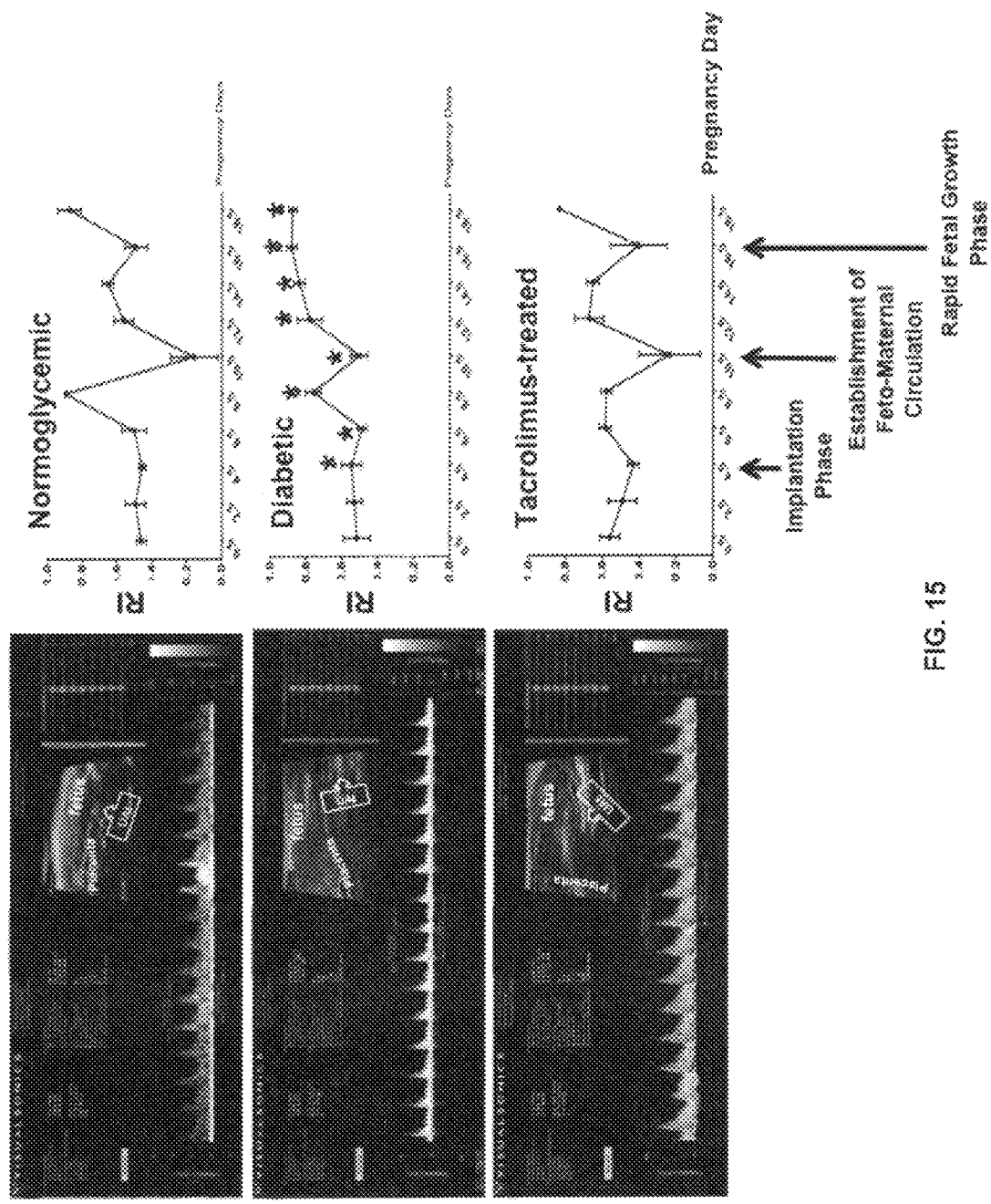
FIG. 15 shows a schematic representation of real-time Pulse Wave Doppler (PWD) tracing of maternal uterine arterial (UAt) blood flow velocity. Multiple implantation sites (3-5) from each of 5-7 pregnant mice were scanned per time point. Images in the microultrasound tracing represent the correct location of the ultrasound probe with the angle of the Doppler beam was kept below 30° for a typical acquisition of the waveform characteristics of arterial blood flow. *P<0.05 between diabetic and the tacrolimus-treated and their normoglycemic control at given time point. Data represented in the graph are mean±SEM. n=5-7.

Tacrolimus also maintained fetal viability and inhibited IUGR development in 88% of all treated pregnant diabetic mice. As shown in FIG. 14A, 68% of near-term pups of diabetic dams are IUGR. The short term administration of tacrolimus rescued 88% of pups born to diabetic dams from inflammatory-mediated growth restriction. The presented evidence demonstrated a direct cause-effect relationship between aberrant maternal IFN-γ-mediated proinflammatory uterine/decidual milieu and the development of IUGR and fetal demise in the diabetic and obese subjects. The reduction in fetal demise and IUGR among pups born to diabetic mice (FIGS. 14A and 14B) correlated with tacrolimus-mediated inhibition of a wide range of IFN-γ-induced proinflammatory cytokines during pregnancy. At the administered dose and timing, tacrolimus proved to be useful in reducing the risk of inflammation-mediated fetal growth retardation linked to maternal vascular maladaptation during pregnancy. Interferon-gamma has a physiological role in promoting gestational changes such a reducing vasoactivity in the decidual arteries during phases of placental and fetal growth in normal pregnancy. It is widely held that IUGR in diabetic pregnancy in mice and diabetic humans alike is linked to significantly impaired decidual artery remodeling caused by the proliferation of non-functional immature subsets of NK cells that is believed to be linked to gestational immune maladaptation developing early in pregnancy (Burke et al. Placenta 2011 32(12):949-955). With inadequate placental perfusion and lack of supply of nutrients, the offspring experienced growth retardation. Diabetic NOD mice with compromised uNK cells had a lower concentration of interferon gamma in the uterus during mid gestation (Leonard et al. Am J Physiol Heart Circ Physiol. 2011 301(4), 1276-85), and experienced all of the resulting complications. The reduction in fetal demise and malformations by the administration of tacrolimus was correlated with sustained decidual arteriolar flow velocity and normalized pattern of vascular resistance to uterine blood flow in 88% of treated pregnant diabetic mice as determined by Doppler waveform measurements (5; p<0.05 compared with vehicle-treated diabetic mice). Of potential clinical importance were the benefits to fetal and maternal health during pregnancy by the use of tacrolimus to immune conditioning diabetic and obese dams prior to conception that proved usefulness in normalizing maternal immune and vascular adaptation during phases of placental and fetal development. The presented evidence demonstrates a direct role for inhibiting maternal production of the proinflammatory cytokines IFN-γ during peri-implantation in restoring normal fetal growth pattern later in pregnancy.

Tacrolimus restored normal uterine vascular adaptation throughout pregnancy in the treated diabetic and obese mice. A schematic representation of real-time Pulse Wave Doppler (PWD) tracing of maternal uterine arterial (UAt) blood flow velocity depicted in FIG. 14 revealed a distinct pattern of reduction in uterine arterial resistance to blood flow that corresponded with three distinct phases of pregnancy, namely during successful implantation at pregnancy day (gd) 4.5, ripening of maternal decidual sinuses and the establishment of feto-maternal circulation during gd 10.5 and a third reduction at the phase of rapid fetal growth during gd 14.5-16.5 in the normoglycemic and the tacrolimus treated mice. Tacrolimus improved uterine arterial hemodynamics to accommodate for fetal demands during pregnancy. Implantation failure and/or delayed implantation and high fetal resorption later in pregnancy in the vehicle-treated diabetic mice were accompanied by a significantly higher resistance to UAt blood flow during gd 4.5 and 16.5 respectively, thereby indicating poor maternal hemodynamic adaptation during the diabetic gestation. Uterine artery resistive index (RI) was calculated for each vessel according to the equation: RI=(Peak Systolic Velocity−Peak Diastolic Velocity)/Peak Systolic Velocity to assess maternal hemodynamic characteristics of tacrolimus-treated versus the normoglycemic and the vehicle-treated diabetic NOD mice.

Figure 16A:
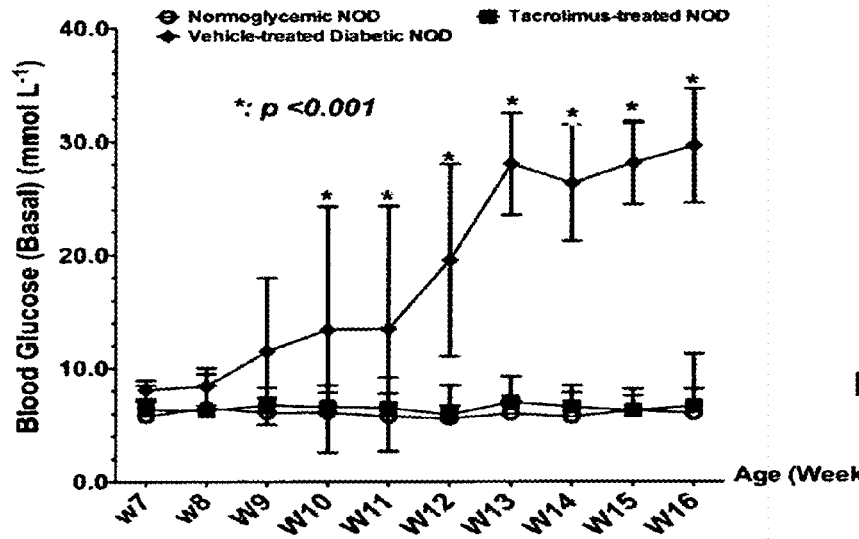
FIGS. 16A and 16B show results of tacrolimus preventing glucose intolerance and restoring normal glucose homeostasis in treated diabetic (FIG. 16A) and obese (FIG. 16B) mice.
Figure 16B:
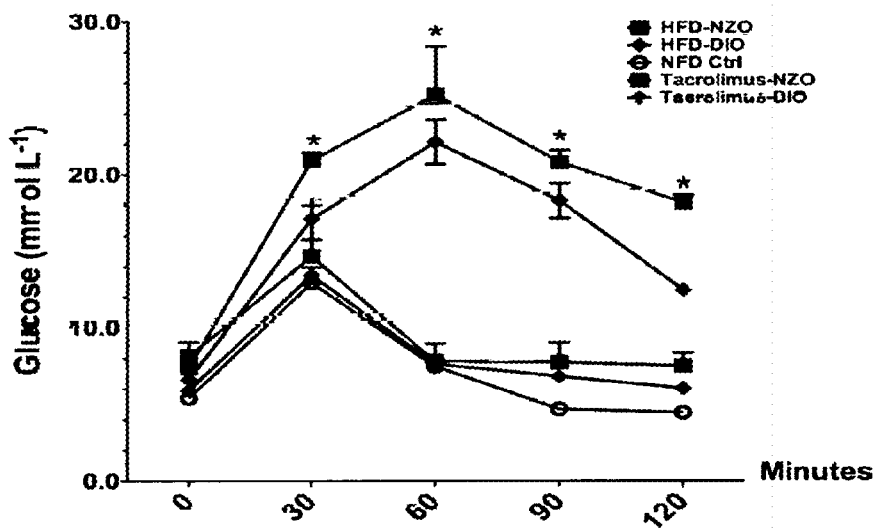
Figure 17A:
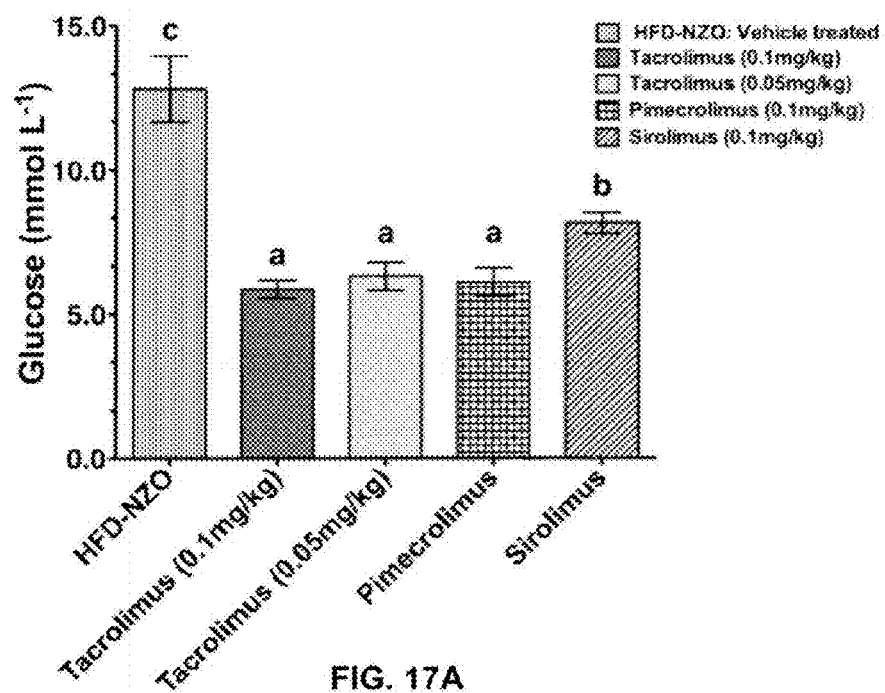
FIGS. 17A, 17B, and 17C respectively demonstrate beneficial effects of short-term administration of macrolide drugs on fasting serum glucose levels, fasting serum insulin levels and preventing/reducing glucose intolerance in NZO mice fed a high fat diet (60% calories from fat) for 9 weeks. Female mice were administered tacrolimus (0.1 mg/kg or 0.05 mg/kg, n=6/group), vehicle (n=10), pimecrolimus (0.1 mg/kg, n=6) or sirolimus (0.1 mg/kg, n=6) subcutaneously every other day for 3 weeks. Treatments significantly improved insulin secretion in response to a hyperglycemic challenge and restored glucose homeostasis compared to vehicle-treated control mice.

Tacrolimus also prevented glucose intolerance and restored normal glucose homeostasis in treated diabetic and obese mice. As shown in FIG. 16A, the group mean graphic representation of weekly non-fasting blood glucose tracing in vehicle-treated versus the tacrolimus-treated diabetic NOD mice and their normoglycemic controls indicated tacrolimus to be effective in restoring normal glycemic phenotype in an autoimmune diabetic host despite the relatively short administration schedule and lower than the clinically recommended dosing. Mice with blood glucose values of >10.0 mM/L at the age of 9-10 weeks and body weight values of >2SD above their normal controls (see the graphic representation of the body weight changes in FIG. 16A) were at 20 times higher risk of developing diabetes later in life. FIG. 16B shows the outcome of a glucose tolerance test after the short-term administration of tacrolimus to the 60% high fat fed NZO and DIO mice. Short term administration of tacrolimus normalized fasting basal serum glucose concentrations (FIG. 17A), and significantly reduced fasting basal serum insulin concentrations (FIG.

Figure 17B:
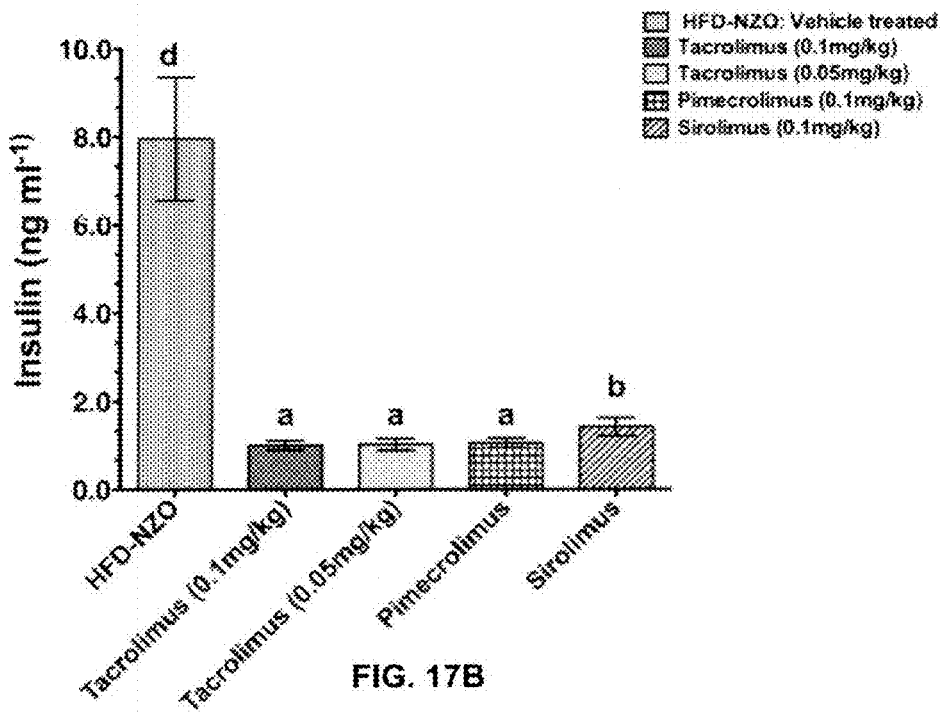
Figure 17C:
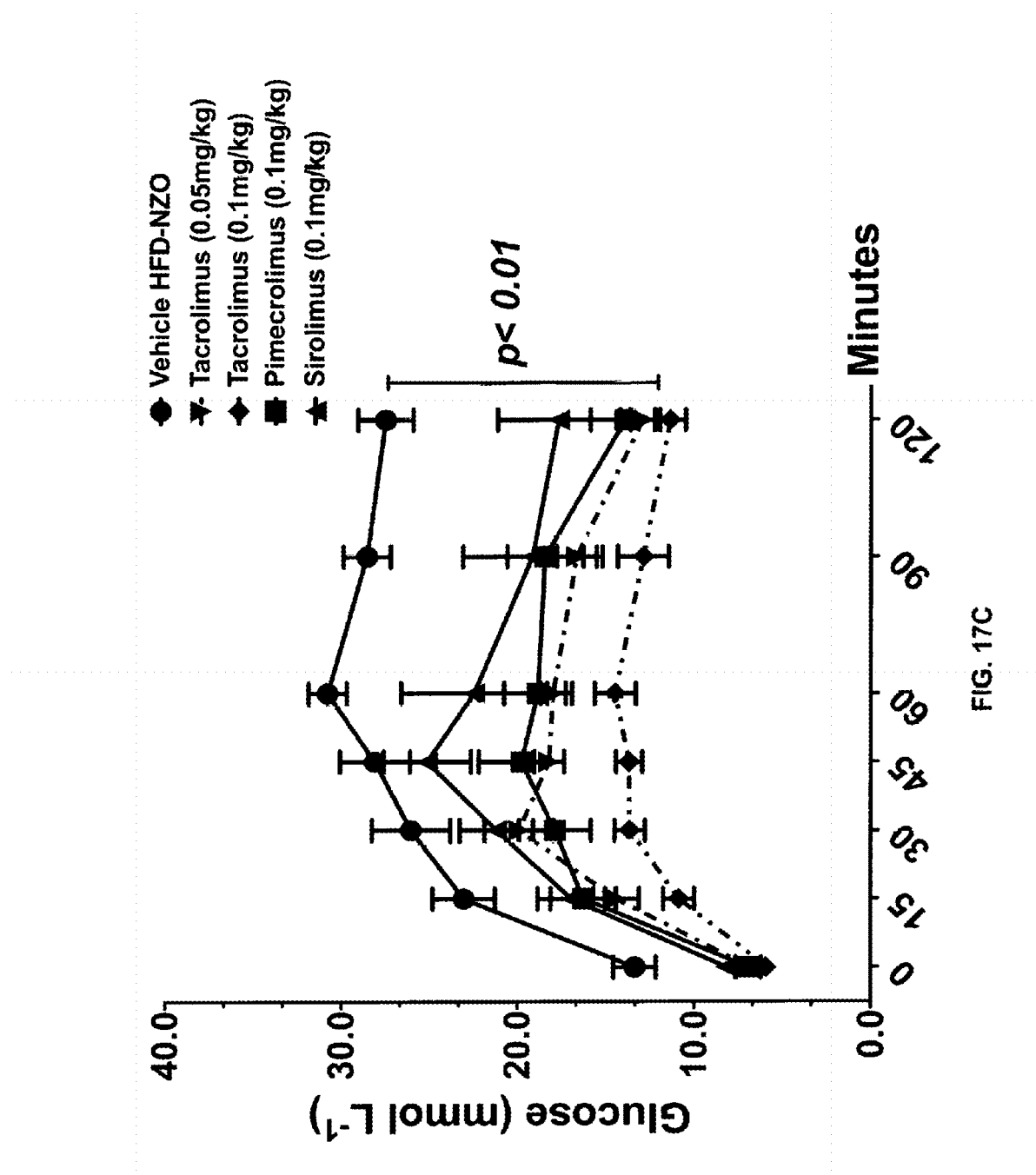

17B) compared to vehicle-treated control NZO-mice fed a 60% high fat diet. Other macrolide drugs, sirolimus and pimecrolimus, benefited glycemic control in these mice at equivalent doses to tacrolimus (0.1 mg/kg), and maintained low fasting basal serum glucose and insulin levels (FIGS. 17B and 17C) in female NZO mice continuously fed a high fat diet. Both drugs also significantly reduced glucose intolerance although to a lesser degree than tacrolimus (FIG. 17C; p=0.0001). Tacrolimus restored normal glucose tolerance in all treated type 2 diabetic and obese mice. Glucose intolerance in the obese and type 2 diabetic subjects is due to an aberrant activation of the peripheral immune system primarily resulting from a fatty-tissue mediated autoimmune response to chronic high calorie intake. While not be limited to any particular mechanism of action, it is believed that the normal glucose tolerance maintained in tacrolimus-treated mice after the initial short term administration is likely related to the observed drug effect on body mass gain in all treated NZO and DIO female mice.

Figure 18A:
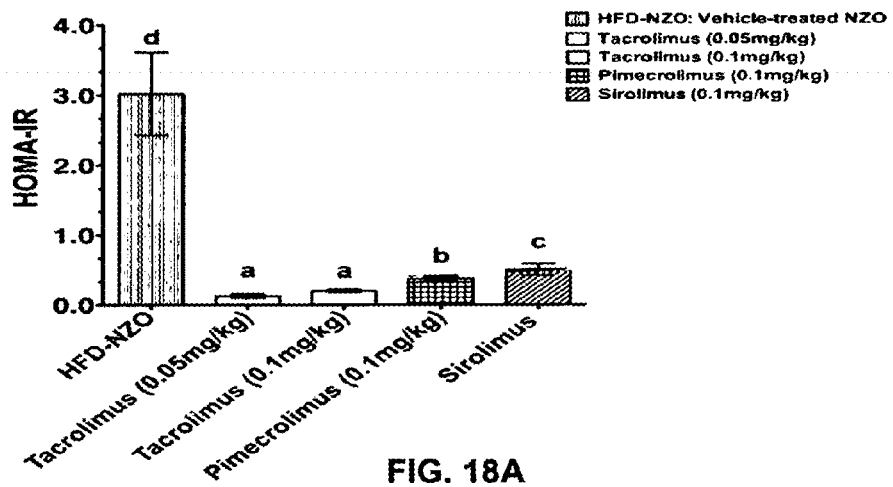
FIGS. 18A to 18C show that macrolide drugs reduced insulin resistance and restored pancreatic β-cell function in the type 2 diabetes NZO mouse model fed a continuous high fat (60% of calories from fat) diet for 12 weeks. Female mice were administered tacrolimus (0.1 mg/kg or 0.05 mg/kg, n=6/group), vehicle (n=10), pimecrolimus (0.1 mg/kg, n=6) or sirolimus (0.1 mg/kg, n=6) subcutaneously every other day for 3 weeks. Treatments significantly improved HOMA-IR (p<0.001) (FIG. 18A), HOMA-B (p<0.05) (FIG. 18B) and insulin sensitivity index (Si) (p<0.01) (FIG. 18C) compared to vehicle-treated controls.
Figure 18B:
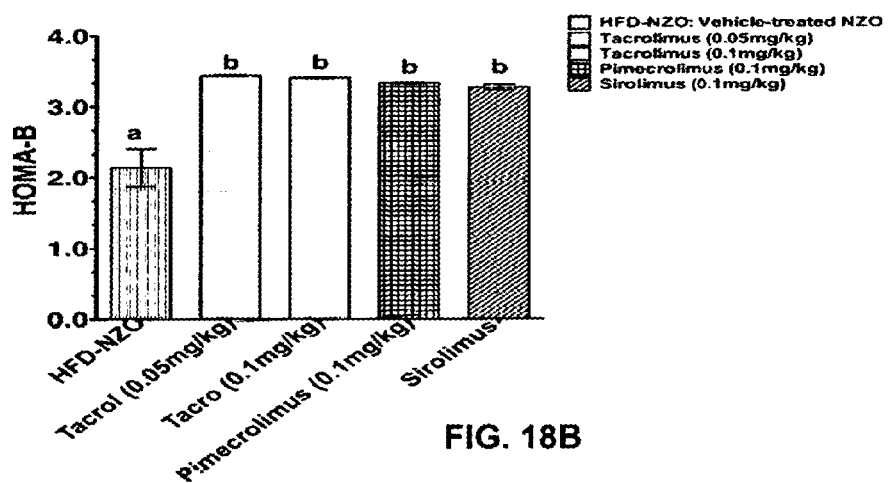
Figure 18C:
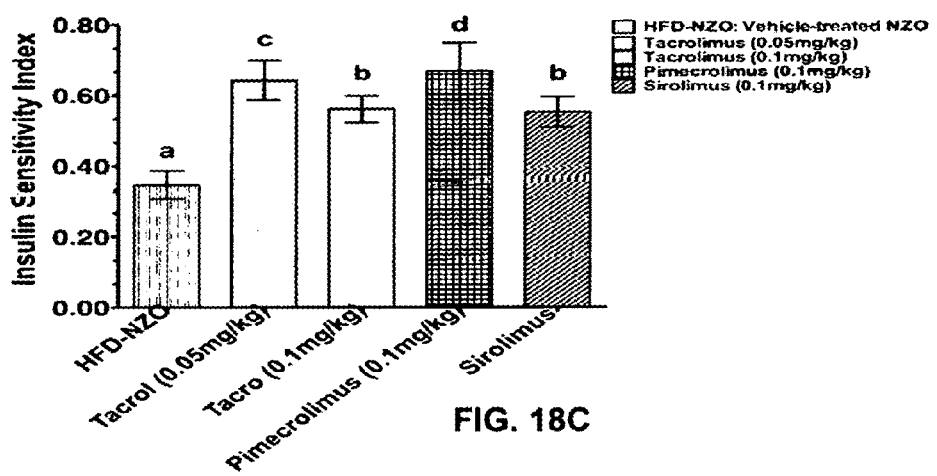

Insulin is released from pancreatic β-cells after eating and stimulates the uptake of glucose into peripheral tissues while inhibiting glucose release from the liver. Insulin resistance is a hallmark of type II diabetes and is the inability of insulin to effectively stimulate uptake of glucose by peripheral tissues. Homeostatic model assessment (HOMA) is an estimate of insulin sensitivity and pancreatic β-cell function (Wallace et al. Diabetes Care. 2004 27(6), 29B.3.5-29B.3.22) and is indicative of the efficacy of this process. Short term administration of macrolide drugs, including tacrolimus, sirolimus and pimecrolimus, in type II diabetic NZO mice significantly reduced insulin resistance (FIG. 18 A), enhanced pancreatic β-cell function (FIG. 18B) and enhanced insulin sensitivity (FIG. 18C).

Figure 19A:
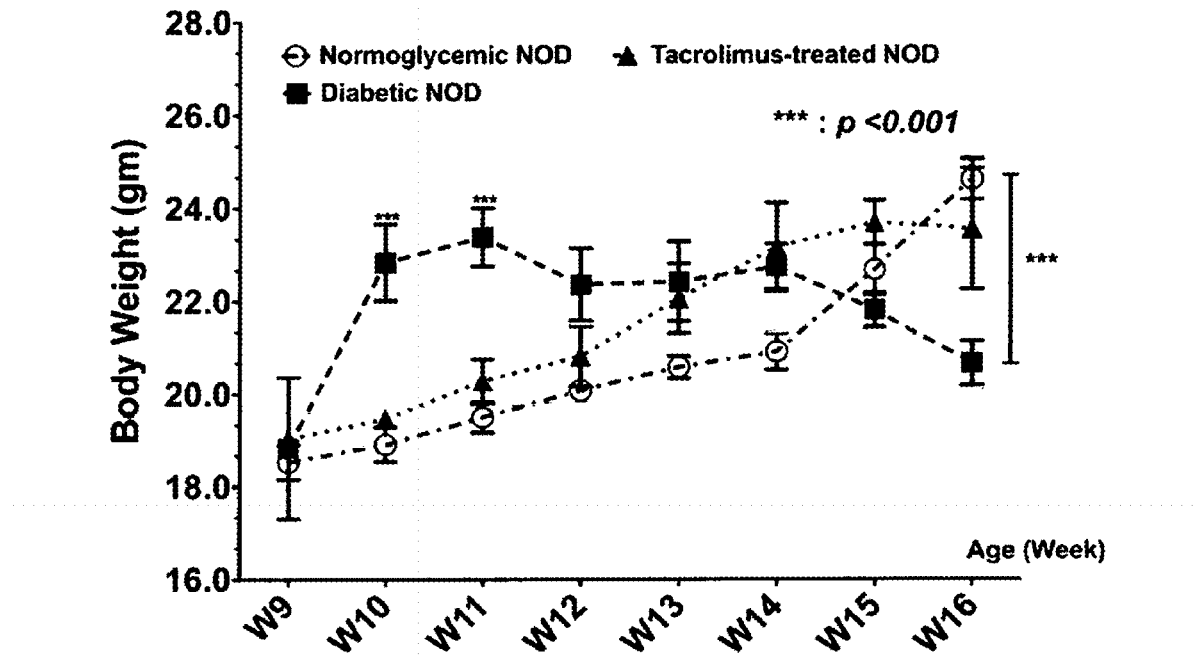
FIGS. 19A and 19B show results of tacrolimus normalizing weight gain in treated diabetic (FIG. 19A) and obese (FIG. 19B) mice. Loss of body mass is among the health risk in type1 diabetes whereas uncontrolled gain of body weight is a major hurdle to IVF success in obese and type2 diabetic women.

Macrolide immunosuppressants also normalized weight gain in treated diabetic and obese mice. Loss of body mass is one of the health risks in type 1 diabetes whereas uncontrolled gain of body weight is a major hurdle to IVF success in obese and type 2 diabetic women. The demonstrated efficacy of tacrolimus in normalizing weight gain in the diabetic and obese mice has a likely added value to the restored normal pregnancy pattern and the prevention of pregnancy-related complications observed in these three mouse models. Further, this demonstrated efficacy is indicative of a role for tacrolimus in restoring normal energy balance during hyper-metabolic states. As shown in FIG. 19A, treated diabetic and prediabetic mice maintained normal body weight gain throughout the study period after the short-term administration of tacrolimus. As shown in the representative graphic representation of body weight changes in the tacrolimus-treated versus vehicle-treated diabetic and their normoglycemic control mice, data herein have identified that mice with body weight values >2 SD (triple asterisk) above their age-matched control during the pre-diabetic stage were at higher risk (20-fold) of developing diabetes later in life (see the graphic representation of blood glucose in these mice).

Figure 20:
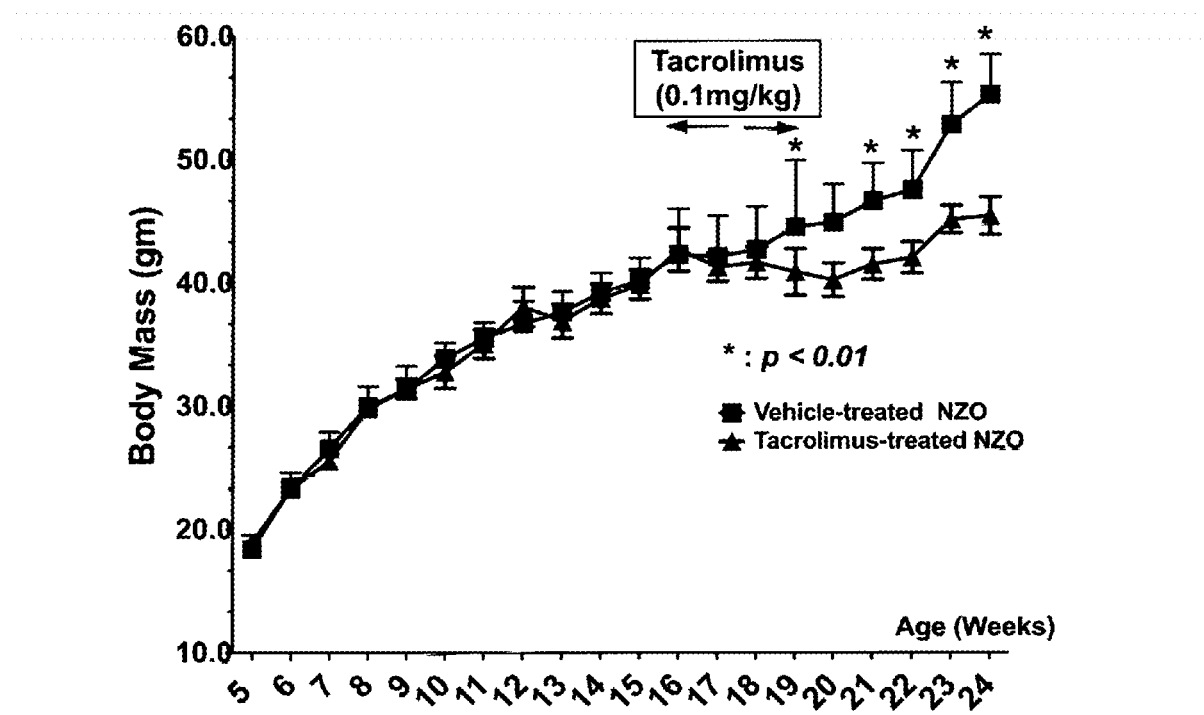
FIG. 20 shows that short term administration of tacrolimus induced weight loss in grossly obese and glucose intolerant NZO female mice chronically fed a high fat diet (60% calories from fat) for 24 weeks. Data shown are mean±SEM of changes in body mass in mice administered tacrolimus (0.1 mg/kg every other day) for four weeks starting at week 16 (N=10/group). Statistical difference between groups was measured by one-way ANOVA at 95% confidence.

Furthermore, short term administration of tacrolimus in very obese female NZO mice fed a high fat diet for two weeks induced a significant weight loss relative to vehicle-treated female NZO mice (FIG. 20; asterisks indicate p<0.05). These mice were administered tacrolimus for four weeks instead of three weeks as in other experiments. This week increase in drug regimen was due to a delay in the treated animals of glucose tolerance returning to a more normal profile.

Figure 19B:
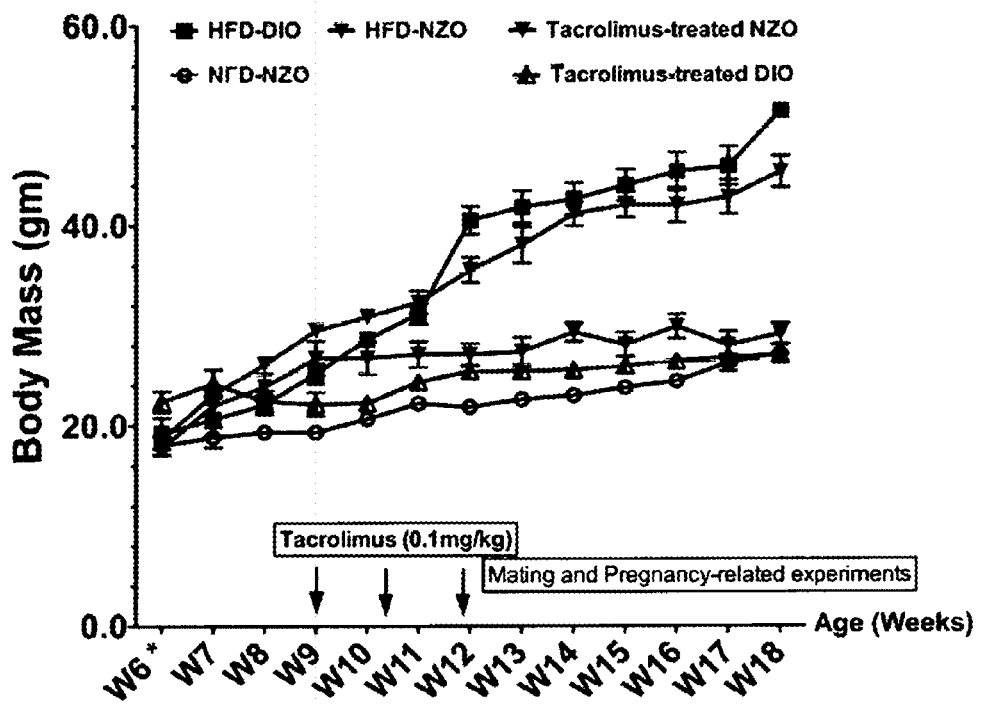
Figure 21:
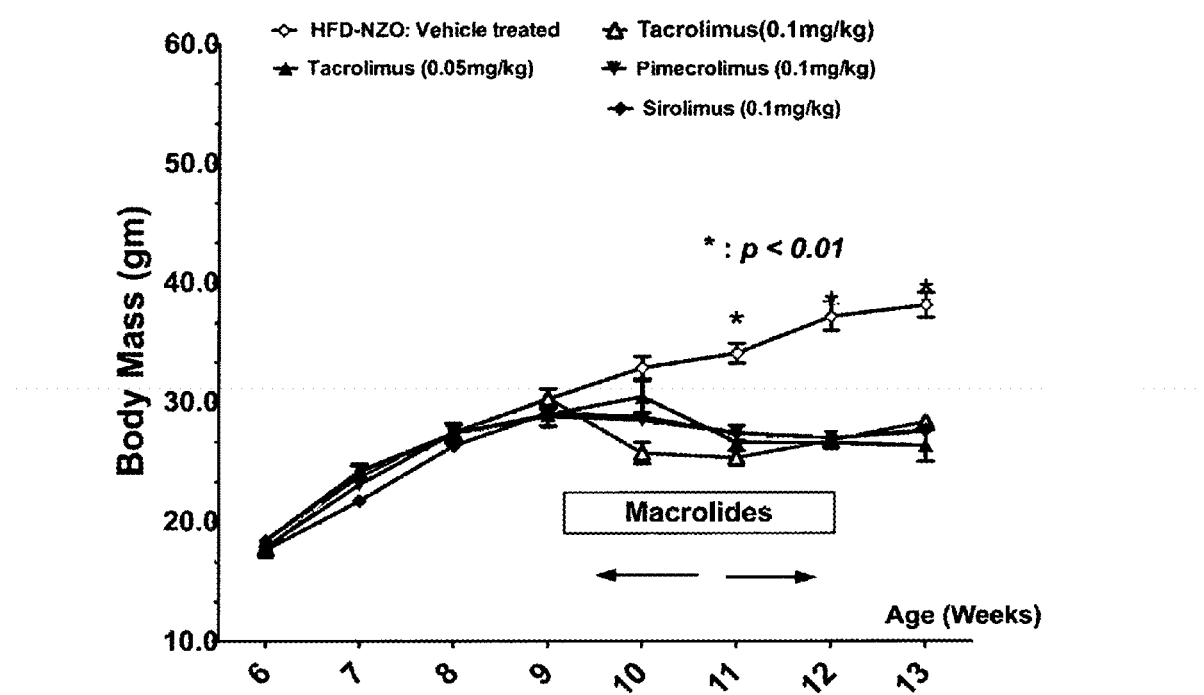
FIG. 21 shows short term administration of various macrolide drugs induced weight loss in NZO mouse model of type 2 diabetes. Tacrolimus (0.05 or 0.1 mg/kg, N=6), pimecrolimus (0.1 mg/kg; N=6), or sirolimus (0.1 mg/kg; N=6) given subcutaneously every other day for three weeks significantly induced weight loss in female NZO mice fed a continuous high fat diet (60% calories from fat) for 9 weeks compared to vehicle treated controls (N=10) (p<0.001 where * noted).

In additional experiments, other macrolide drugs, pimecrolimus and sirolimus, also induced statistically significant weight loss in female NZO mice fed a continuous high fat diet (FIG. 21; asterisks represent p<0.01 relative to vehicle-treated control mice). The efficacy of tacrolimus and other macrolide drugs to prevent weight gain or induce weight loss in the treated mice is believed to be indicative of their administration aiding in long-term prevention or correction of diabetes development in the treated mice. As shown in FIG. 19B, short-term administration of tacrolimus to the 60% high fat fed NZO or DIO mice prevented body weight gain for seven consecutive weeks after the initial administration in all treated mice. Characteristically the mass of the visceral fat in all treated mice was also significantly lower. Reduction in body mass in treated NZO or DIO mice is believed to be a key milestone in the restoration of normal glucose tolerance and fertility outcome in animal models of type 2 diabetes, PCOS and the metabolic syndrome.

Tacrolimus also restored normal lipid profile in all treated diabetic and obese mice fed with 60% fat for 12 weeks. Normal serum levels of triglycerides (FIG. 22A and FIG. 22B), total cholesterol (FIG. 22C and FIG. 22D), high-density lipoprotein (HDL) cholesterol (FIG. 22E and FIG. 22F) and lipid ratio representing the overall lipid profile (FIG. 22G and FIG. 22H) were obtained after the administration of tacrolimus to the diabetic and obese mice despite their continued high fat calorie intake. These data further support the beneficial effect of tacrolimus in restoring normal ovarian functions, body mass gain and energy expenditure in treated obese and diabetic mice as well as in treating dyslipidemia in a subject in need thereof.

These studies are indicative of administration of macrolide agents such as tacrolimus, pimecrolimus and sirolimus (preferably tacrolimus as it unexpectedly exhibits greater activity) at doses as low as 0.05 and 0.1 mg/kg being effective in increasing fertility and/or inhibiting pregnancy failure. These studies are also indicative of administration of macrolide agents such as tacrolimus, pimecrolimus and sirolimus (preferably tacrolimus as it unexpectedly exhibits greater activity) at doses as low as 0.05 and 0.1 mg/kg being effective at restoring glucose tolerance and/or preventing glucose intolerance and/or maintaining glucose homeostasis and/or increasing insulin sensitivity and/or preventing weight gain and/or inducing or enhancing weight loss in an individual in need thereof. Administration of the macrolide agent can be relatively short term and can typically last for 6 months or less, for example 4 to 8 weeks. In one embodiment, assuming the individual has a menstrual cycle length of 28-32 days, the dosing regimen for increasing fertility and/or inhibiting pregnancy failure comprises an initial 10 mg/kg loading dose followed by 0.1-1.0 mg/kg dose every other day for three weeks starting at the end of the first week of her menstrual cycle for at least three cycles. In one embodiment, this dosing regimen is continued for 6 cycles. As will be understood by the skilled artisan upon reading this disclosure, however, alternative dosing regimens can be determined based upon the severity of an individual's host immune activation as determined by their blood and uterine biomarker assays. Once pregnancy is confirmed by abdominal ultrasound administration will be stopped. It is expected that this dosing regimen will be particularly useful in autoimmune diabetes prone individuals known to have pregnancy complications and low fecundity efficiently promoting pregnancy, improving maternal glycemic control and maintaining maternal and fetal health. Further, it is expected this short-term dosing regimen will promote maternal and fetal health in other individuals genetically susceptible to develop early and late autoimmune pregnancy complications in a timely manner. According to the FDA, calculating a human equivalent dose from animal studies needs to done by normalizing to bovine serum albumin (Center for Drug Evaluation and Research, Center for Biologics Evaluation and Research. (2002) *Estimating the safe starting dose in clinical trials for therapeutics in adult healthy volunteers*, U.S. Food and Drug Administration, Rockville, Md., USA). This can be done using $K_m$ factors where the Humand equivalent dose (HED)=animal dose in mg/kg multiplied by animal Km/human $K_m$ (Reagan-Shaw et al. FASEB J. 2008 March; 22(3):659-61). The HED for a dose of 0.05 mg/kg in a mouse is equal to 0.05 mg/kg×3/37=0.004 mg/kg in a human. The recommended starting dose of tacrolimus (Prograf) is 0.03-0.05 mg/kg/day in kidney and liver transplant patients and 0.01 mg/kg/day in heart transplant patients given as a continuous IV infusion while for oral delivery it is 0.1 to 0.3 mg/kg/day. This is a seven and seventy-five-fold difference, respectively, dependent upon delivery mode. A clinical study using 0.1 mg/kg once-daily extended release formulation of tacrolimus (Advagraf) found an average tacrolimus trough blood concentration of 6.4 ng/ml. This represents over a ten-fold difference based upon the efficacious blood concentration.

A study using subcutaneous tacrolimus in rats at 0.1 mg/kg every other day (q2d) resulted in a maximal blood concentration of 0.6 nanograms/ml (Yanchar et al. Transplantation. 1996 61(4):630-4). The smallest currently available tacrolimus dose is a 0.5 mg capsule and a single oral dose of 0.5 mg tacrolimus results in a maximal blood concentration in humans of 4.6 ng/ml (Mathew et al. Clinical Therapeutics. 2011 33(9):1105-1119). This represents over a seven-fold difference based upon the efficacious blood concentration of tacrolimus in experiments disclosed herein. A dose of 0.1 mg/kg in rats represents does of 0.2 mg/kg in mice, based upon a rat $K_m$=6. This is a four-fold higher dose (0.2 mg/kg) than used in experiments disclosed herein. Therefore, the likely blood concentration from the dose regimen described herein would be four-fold lower (i.e. 0.15 ng/ml blood concentration) and represents an even greater exposure difference (28-fold to 38-fold) compared to existing tacrolimus dose forms for humans. Thus, experiments disclosed herein indicate that a substantially lower dose of macrolide agent such as tacrolimus than routinely administered to date may be useful in the methods of the present invention. By "substantially lower dose" or "low dose therapy" for purposes of the present invention, it is meant a dose of macrolide agent at least 2-fold lower, more preferably at least 4-fold lower, more preferably at least 10-fold lower, than the recommended starting doses of tacrolimus (Prograf) when administered for kidney and liver transplant or heart transplant.

While not wishing to be bound to any theory, it is believed that tacrolimus achieves at least some of these results through suppressing the production of the aberrantly induced IFN-γ by inhibiting expression of IFN-γ or a downstream IFN-γ-stimulated gene such as, but not limited to MUC1 or PAISγ. In addition, administration of a macrolide immunosuppressant in accordance with the present invention may induce LIF expression and/or phosphorylation of NFkBp65 and STAT3.

The present invention also provides compositions for enhancing fertility and/or inhibiting pregnancy failure in an individual need thereof. Such compositions may also be used to restore glucose tolerance and/or prevent glucose intolerance and/or maintain glucose homeostasis and/or increase insulin sensitivity and/or prevent weight gain and/ or induce or enhance weight loss and/or inhibit dyslipidemia in an individual in need thereof. In one embodiment, the composition is administered to an individual with an autoimmune condition. In one embodiment, the individual is hyperglycemic. In one embodiment, the individual has type 1 diabetes. In another embodiment, the individual has type 2 diabetes. In one embodiment, the individual is obese.

Compositions of the present invention comprise an effective amount of a pharmaceutically active ingredient which inhibits expression of IFN-γ or a downstream IFN-γ-stimulated gene. In one embodiment, the pharmaceutically active ingredient is a macrolide immunosuppressant. In one embodiment, the macrolide immunosuppressant is tacrolimus, pimecrolimus or sirolimus. In one embodiment, the macrolide immunosuppressant is tacrolimus.

Compositions of the present invention may further comprise a pharmaceutically active ingredient for treatment of the autoimmune condition. For example, in one embodiment, a combination therapy of metformin and an inhibitor of expression of IFN-γ or a downstream IFN-γ-stimulated gene may be administered.

The compositions may be administered by various routes including, but not limited to, orally, transdermally, dermally, intravenously, intramuscularly, intraperitoneally, topically, subcutaneously, rectally, intravaginally or intrauterine (e.g., via a ring or intrauterine device (IUD)) intraocularly, sublingually, buccally, intranasally or via inhalation. Oral, intravenous or dermal administration may be preferred. The formulation and route of administration as well as the dose and frequency of administration can be selected routinely by those skilled in the art based upon the severity of the condition being treated, as well as patient-specific factors such as age, weight and the like.

Accordingly, for purposes of the present invention, the therapeutic compound, namely the inhibitor of expression of IFN-γ or a downstream IFN-γ-stimulated gene, in one embodiment tacrolimus, can be administered in a pharmaceutically acceptable vehicle.

As used herein "pharmaceutically acceptable vehicle" includes any and all solvents, excipients, dispersion media, coatings, antibacterial and antifungal agents, isotonic and absorption delaying agents, and the like which are compatible with the activity of the therapeutic compound and are physiologically acceptable to a subject. An example of a pharmaceutically acceptable vehicle is buffered normal saline (0.15 M NaCl). The use of such media and agents for pharmaceutically active substances is well known in the art. Except insofar as any conventional medium or agent is incompatible with the therapeutic compound, use thereof in the compositions suitable for pharmaceutical administration is contemplated. Supplementary active compounds can also be incorporated into the compositions.

As evidenced by Mordenti (*J. Pharm. Sci.* 1986 75(11): 1028-40) and similar articles, dosage forms for animals such as, for example, rats can be and are widely used directly to establish dosage levels in therapeutic applications in higher mammals, including humans. In particular, the biochemical cascade initiated by many physiological processes and conditions is generally accepted to be identical in mammalian species (see, e.g., Mattson et al. Neurotrauma 1994 11(1): 3-33; Higashi et al. Neuropathol. Appl. Neurobiol. 1995 21:480-483). In light of this, pharmacological agents that are efficacious in animal models such as those described herein are believed to be predictive of clinical efficacy in humans, after appropriate adjustment of dosage.

The invention also provides a combination therapy in which two or more therapeutic compounds are administered. Each of the therapeutic compounds may be administered by the same route or by a different route. Also, the compounds may be administered either at the same time (i.e., simultaneously) or each at different times. In some treatment regimes it may be beneficial to administer one of the compounds more or less frequently than the other.

Dispersions comprising the therapeutic compound can be prepared in glycerol, liquid polyethylene glycols, and mixtures thereof and in oils. Under ordinary conditions of storage and use, these preparations may contain a preservative to prevent the growth of microorganisms. Pharmaceutical compositions suitable for injectable use include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, liquid polyethylene glycol, and the like), suitable mixtures thereof, and oils (e.g. vegetable oil). The proper fluidity can be maintained, for example, by the use of a coating such as lecithin, by the maintenance of the required particle size in the case of dispersion, and by the use of surfactants.

Sterile injectable solutions can be prepared by incorporating the therapeutic compound in the required amount in an appropriate solvent with one or a combination of ingredients enumerated above, as required, followed by filter sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient (i.e., the therapeutic compound) optionally plus any additional desired ingredient from a previously sterile-filtered solution thereof.

Solid dosage forms for oral administration include ingestible capsules, tablets, pills, lollipops, powders, granules, elixirs, suspensions, syrups, wafers, buccal tablets, troches, and the like. In such solid dosage forms the active compound is mixed with at least one inert, pharmaceutically acceptable excipient or diluent or assimilable edible vehicle such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof, or incorporated directly into the subject's diet. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The percentage of the therapeutic compound in the compositions and preparations may, of course, be varied.

The amount of the therapeutic compound in such therapeutically useful compositions is such that a suitable dosage will be obtained.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, ground nut corn, germ olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Therapeutic compounds can be administered in time-release or depot form, to obtain sustained release of the therapeutic compounds over time. The therapeutic compounds of the invention can also be administered transdermally (e.g., by providing the therapeutic compound, with a suitable vehicle, in patch form).

The present invention is further illustrated by the following nonlimiting examples.

The following disclosure should not be construed as limiting the invention in any way. One of skill in the art will appreciate that numerous modifications, combinations, rearrangements, etc. are possible without exceeding the scope of the invention. While this invention has been described with an emphasis upon various embodiments, it will be understood by those of ordinary skill in the art that variations of the disclosed embodiments can be used, and that it is intended that the invention can be practiced otherwise than as specifically described and/or claimed herein.

EXAMPLES

Example 1

Animals

All animal procedures complied with protocols approved by the University Animal Care Committee of Queen's University. One hundred seventy-five of the type 1 diabetic NOD/ShiLtJ, twenty of the type 2 diabetic NONcNZO10/LtJ and twenty-five of the diet-induced obese C57BL/6J and fifty BALBc female mice were purchased from the Jackson Laboratories (Bar Harbor, Me., USA) were housed under standard husbandry in the Central Animal Facility at Queen's University in Kingston Ontario. All mice were brought to the animal housing facility at the age of 7 weeks. NOD/ShiLtJ female mice, referred to as NOD, were used as a model of autoimmune mediated type 1 diabetes and were fed with 20% fortified protein pellet diet (Co-op Feeds, Saskatoon, Canada). The NONcNZO10/LtJ, referred to as NZO, were used as a model of obesity mediated type 1 diabetes and the C57BL6, referred to as DIO, were both fed with 60% fat for 12 weeks starting at the age of 7 weeks as described by Ortlepp et al. (Eur J Clin Invest 2000 30:195-

202), Andrikopoulos et al. (2001. The New Zealand obese mouse: a polygenic model of type 2 diabetes. In Animal Models of Diabetes: A Primer. Sima A A F, Shafrir E, Eds. Amsterdam, Harwood Academic. pp. 171-84) and Leiter and Reifsnyder (Diabetes 2004 53 Suppl 1:S4-11). To exclude mouse-strain individual variations in examining endometrial/decidual parameters, the remaining B6 females and the BALBc mice were used as additional normal controls. All animals were individually housed at ambient temperature with 12 hr dark/12 hr light cycles and were allowed free access to their pellet diet and tab water ad libitum and all animal cages were maintained with wood chip beddings.

Example 2

Blood Glucose Monitoring

Through the use of Ultra Glucosemeter (Accu-Chek Aviva/Roche Diagnostic, Laval, Quebec, Canada) blood glucose levels for all mice were monitored via tail venipuncture once a week on a regular basis beginning at the age of 8 weeks. Animals with non-fasting or those having blood glucose values ≥14.9 mmol/L after the glucose challenge (glucose tolerance) test were identified as diabetic. All normoglycemic animals had blood glucose values of less than 10.0 mM/L.

Example 3

Vaginal Smear Sampling and Identification of Specific Stages of the Estrous Cycle in Nulliparous Animals Using Papanicolaou's staining kit (Sigma Aldrich, Oakville, Ontario, Canada), staining of vaginal smears obtained between 09:00-10:00 AM was performed to identify the phases of the estrous cycle and to establish the individual animal cycling pattern as previously described (Koss L. G (Ed): The Papanicolaou Stain. In Diagnostic Cytology and its Histopathological Bases. 4$^{th}$ Edit. Koss, Leopold; Melamed and Myron R. Eds. J.B. Lippincott Williams & Wilkins (LWW), Philadelphia. 1992; Vol. 2: 1211-1221). Blood and virgin uteri were collected from nulliparous diabetic NOD females, at the proestrus, estrus and the metestrus phase, respectively, after four weeks in diabetes. Blood and uteri were also collected from age-matched, tacrolimus-treated nulliparous NOD mice immediately after completing the treatment schedule.

Example 4

Tacrolimus Dosage and Schedule in the NOD Mice

Fifty four NOD mice at the prediabetic and early diabetic stages were carefully selected to match the criteria of being 2 standard deviation heavier in body weight than their age-matched normoglycemic control mice and having blood glucose value of >14.9 mM/1 during the glucose tolerance test. The selected mice were 9 weeks old and were treated with 0.1 mg/kg q2d of tacrolimus (Prograf (5 mg/ml), Astellas) subcutaneously administered in 0.2 ml saline for three weeks after which animals were mated to males of the same strain (See FIG. 1). Vehicle (0.2 ml saline, s.q.) treated hyperglycemic NOD female mice were allowed two weeks in diabetes before they were mated to males of the same strain. Facial (mandibular) venous blood samples were collected from treated animals at 24 and 48 hours between injections and at pregnancy days 0.5, 2.5, 4.5, 6.5, 8.5, 10.5, 12.5, 14.5, 16.5 and 18.5 respectively following a standard procedure for facial bleed in mice (Golde et al Lab Anim (NY) 2005 34:39-43).

Example 5

Generation of Type 2 Diabetic NZO and DIO C57BL6

Figure 2:
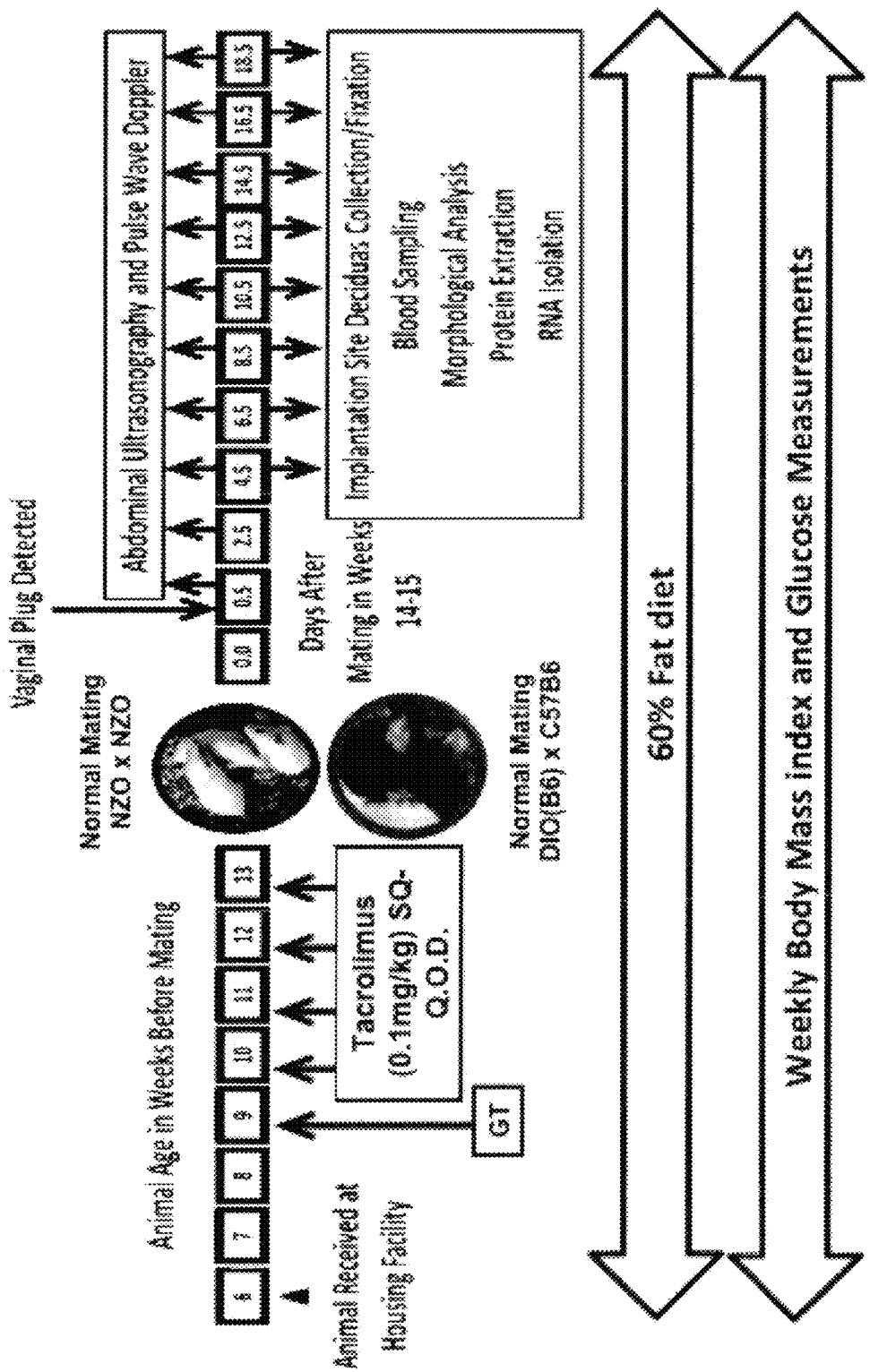
FIG. 2 is a flow chart showing the experimental design and dosing schedule for tacrolimus used in the New Zealand (NZO) mouse model and diet-induced obesity (DIO) model of Type 2 diabetes and metabolic syndrome. All mice were kept on 60% high fat diet for the entire period of the study.

Twenty NZO and DIO/B6 female mice were maintained on a high fat diet consisted of 60% kcal fat, 20% kcal protein and 20% kcal carbohydrate, with a total energy mass of 5.24 kcal/gm (D12492, Research Diets Inc.; Cedarlane Laboratories, Burlington, Ontario, Canada) starting at 7 weeks of age and maintained on the diet for a total of 12 weeks of study period during which their weekly body weight changes and non-fasting blood glucose values were recorded. Mice which became obese as defined by having a Body mass index (BMI) value of 30, and tested positive for glucose intolerance were selected for an initial treatment episode with tacrolimus after being fed for four weeks with the high fat diet (See FIG. 2). Tacrolimus (Prograf (5 mg/ml), Astellas) was administered subcutaneously in a dose of 0.1 mg/kg q2d in 0.2 ml saline for three weeks to the obese and glucose intolerant NZO and DIO mice starting at the age of 10 weeks after which animals were mated to males of the same strain and pregnancy was dated from the morning of the positive detection of vaginal (copulation) plug. See FIG. 2. Facial (mandibular) venous blood samples were collected from treated animals at 24 and 48 hours between injections and at pregnancy days 0.5, 2.5, 4.5, 6.5, 8.5, 10.5, 12.5, 14.5, 16.5 and 18.5, respectively, following a standard procedure for facial bleed in mice (Golde et al. Lab Anim (NY) 2005 34:39-43). A lean cohort of control B6 and BALBc mice was fed with a regular 10 kcal % control chow diet containing the same protein content as the high fat diet with a total energy mass of 3.1 kcal/g (D12450Bi, Cedarlane, Ontario).

For studies on a grossly obese state, mice were maintained on the 60% high fat diet for 24 weeks starting at 7 weeks of age and designated as being type II diabetic according to methods described above.

For the comparative evaluation of other macrolide drugs to tacrolimus, mice starting at 7 weeks of age were maintained on the high fat diet for a total of 13 weeks of study period. Mice were entered into the experiments when determined to be glucose intolerant as described above. Methods of drug administration and other experimental methods were as described above.

Example 6

Preparation of Pregnant and Pseudo-Pregnant [Bead-Induced Deciduoma (Bid)] Uterine Samples Peri-implantation (E4.5) and post-implantation (E6.5) pregnant and/or pseudopregnant (E4.5bid and E6.5bid) mouse uteri were prepared after mating respectively with fertile and/or vasectomized males as previously described (Herington et al. Endocrinol 2009 150: 4404-4413). The morning of vaginal plug detection was considered as gestational day 0.5 (E0.5 or Gd.0.5). An average number of twenty Concanavalin A(ConA)-coated sepharose beads (average size of 0.1 mm-diameter) (Sigma-Aldrich, Burlington, Ontario, Canada) was injected into the lumen of the left uterine horn of anesthetized animals between hours 13:00 and 16:00 on day 2.5 of pseudopregnancy according to the procedure described by Herington et al. (Endocrinol, 2009 150: 4404-4413). With the use of Ketamine/Xyalzine anesthesia and cardiac puncture, all animals were sacrificed at the age of 16-18 weeks between the morning hours 09:00-11:00. Pregnant and pseudopregnant mice were sacrificed in the morning of days 4.5 and 6.5 of their respective pregnancy. Blood samples were collected from all animals and were let stand for 1 hour at room temperature before isolation of the serum. Serum samples were stored at −80° C. until they were analyzed for their steroid hormones and lipid contents by appropriate laboratory procedures such as radio-immunoassay (RIA) all of which were conducted at the Department of Clinical Chemistry (Kingston General Hospital, Kingston, Ontario, Canada). Ovaries, oviducts and uteri were carefully dissected out of carcasses and were placed in ice-cold phosphate buffered saline (PBS)-containing petri dishes. Under a dissecting microscope, uteri were carefully isolated from their attached uterine tubes, trimmed of all mesenteric fat and were immediately weighed. The numbers of corpora lutea and implantation sites (viable and resorbed) were counted, respectively, from E4.5 and E6.5 pregnant mouse ovaries and uteri. For protein and RNA extraction, virgin uteri and segments of uterine horns containing inter-implantation sites of pregnant and pseudopregnant uteri were transected and snapped frozen in liquid nitrogen.

Example 7

Tacrolimus Assay

Following a standard HPLC-ELS based Mass Spectrometric analytic procedure for quantifying blood concentration of tacrolimus (Taylor et al Clinical Chemistry 1997 43:2189-2190 and Matuszewski et al. Anal. Chem. 2003 75:3019-3030), whole blood samples of treated mice were analyzed for their content of tacrolimus at the Chemistry Department of Queen's University in Kingston Ontario. Briefly, each 100 ul of freshly collected whole blood was precipitated in 300 ul of precipitating solution containing 0.15M Zinc Sulphate in (BDH Chemicals, Toronto, Ontario) 70% Acetonitrile (BDH Chemicals, Toronto, Ontario) and supernatant was isolated after spinning at 13,200 g for 5 minutes at room temperature. The isolated sample supernatants were then loaded onto preconditioned solid-phase extraction (SPE) cartridges (100 mg Sep Pak C18, Waters Limited, Mississauga, Ontario, Canada), sequentially washed with 3 mL of double distilled deionized water, 1 mL 20% methanol in water and 1 mL heptane, and were eluted with 1 mL 50:50 isopropanol:heptane. Eluted samples were dried in an evacuated centrifuge at 45° C. and were reconstituted in 100 μl of 50:50 methanol:water prior to LC-MS/MS analysis. A standard curve was generated using tacrolimus calibration standards prepared in the 50:50 methanol: water solutions of lysed whole blood to attain concentrations of 1.5, 3, 10 and 20 μg/L, respectively. The mobile phase consisted of the following solvents: A: methanol and B: methanol/water (20%/80% v/v) supplemented with 100 μmol/L sodium formate with the following gradient profile: 0-8.5 min: 95-6% B linear; 8.5-9.5 min: 6% B; 9.5-11.0 min: 6-95% B linear; 11.0-14.0 min: 95% B. The mobile phase was filtered through a 0.22 μm membrane filter (Millipore, MA, USA) prior to loading into a heated C18 HPLC column (50×2.1 mm, 5 um particle size) fitted with a Supelco C18 precolumn filter.

Example 8

Serum Lipid and Hormonal Assays

Serum samples from tacrolimus-treated and saline-treated diabetic and obese mice and their normoglycemic control mice were assayed for serum Triglycerides, cholesterol, both total and High-density Lipoprotein (HDL)-conjugated and their lipid ratio, serum estrogen (estradiol (E2), progesterone (P4) and Luteinizing hormone (LH) by Radio-immunoassay (RIA) at the Core laboratories at Kingston General Hospital in Kingston, Ontario. Results are displayed as mean±SEM.

Example 9

Transabdominal Micro-Ultrasonography

Following the procedure described by Mu and Adamson (Am. J. Physiol. Heart Circ. Physiol. 291: H1421-H1428) for comparing patterns of blood flow hemodynamics in the uterine artery, transcutaneous ultrasound biomicroscopy and Doppler waveform recording were collected and analyzed from tacrolimus treated versus the diabetic and obese mice and their normoglycemic control cohort of mated pregnant mice using a microultrasound biomicroscope (Vivo770, Visual Sonic Inc., Toronto, Ontario, Canada) and a 30-40 MHz Real-Time Micro Visualization scanhead transducer operating at two frames per second (RMV704 or 708, VisualSonics Inc). Briefly, mice were lightly anesthetized with inhaled isoflurane (~2.0%) in oxygen delivered by a well-fitted face mask, were positioned in dorsal recumbency position and were taped (Transpore; 3M, Maplewood, Minn.) onto the heated mechanical stage platform with controller temperature set at 36-37° C. throughout the examination. Fur was removed from the ventral side of the lower abdomen using a chemical fur removal gel (Nair; Church & Dwight Co., Inc, Princeton, N.J.) and a layer of pre-warmed coupling gel (Ecogel 100; ECO-MED Pharmaceutical, Mississauga, Ontario, Canada) was applied over the area to be scanned. The sonographer was blinded to the treatment groups. Maternal heart and respiration rates were recorded via a physiological controller unit connected to the mechanical platform. Doppler velocity waveforms were obtained from uterine artery (UAt) two distinct points along its anatomical course, the first position was from its proximal portion near its origin from the common iliac and the second point where it crossed the mesometrium adjacent to the conceptus being analyzed were captured in the brightness mode (B-mode) Doppler imaging with the following parameters: the lowest high-pass filter level used was 100 Hz, 2000 ms display window, Doppler gain of 5.00 dB, the pulsed repetition frequency was between 4 and 48 kHz was set to detect low and high blood flow velocities, respectively and a an angle of <30 degrees between the Doppler beam and the longitudinal axis of the vessel assessed deemed acceptable. Peak systolic velocity (PSV) and end-diastolic velocity (EDV) were calculated from five to seven consecutive cardiac cycles not affected by motion caused by maternal breathing, and the measurements obtained from each of the two locations along the UAt at each time point were subsequently normalized by dividing the average measurement for each time point by the mean values assessed for each conceptus in each dam examined. This normalization was used to facilitate comparison of data obtained from different dams. Systolic and diastolic flow parameters were assessed in the selected point along the course of the uterine artery at 3-5 min intervals and the resistance index (RI=[PSV−EDV]/PSV) was calculated when EDV>0 to measure the pulsatility of arterial blood velocity waveforms.

Example 10

Morphological and Immunohistochemical Analyses

Examination of external morphological features of uteri of pregnant mice, including counts of implantation sites and photography was performed using a computerized dissecting microscope (Leica Diagnostic Instruments, USA) and the image acquisition and analytic software (SPOT 2.2.0). Percentage of peri-implantation embryo loss was calculated as described by Bindali and Kaliwal (Ind. Health, 2002 40:191-197), using the formula:

% Preimplantation loss=[Total number of corpora lutea−Total number of implantation]/Total number of corpora lutea.

Immunohistochemical localization and assessment of microscopic morphological features of implantation and inter-implantation sites in normoglycemic and diabetic NOD mice were performed on methacarn (60% methanol, 30% chloroform and 10% acetic acid)-fixed specimens. Using standard procedure (Mikel U V (Ed): Advanced Laboratory Methods in Histology and Pathology. Armed Forces Institute of Pathology, Washington, D.C., USA: 1994), uterine, decidual and/or inter-implantation site samples were processed into paraffin blocks using an automated tissue processor (Leica ASP300S, USA). Six virgin uteri from each of the designated phases of the estrous cycle, five implantation and inter-implantation sites from E4.5 and E6.5 pregnant normoglycemic (n=7 from each of E4.5 and E6.5 groups) and diabetic (n=10 from each of E4.5 and E6.5 groups) NOD mice were serially sectioned (5 μm thickness) at their centers, and were mounted onto glass slides. Following standard procedures for immunohistochemical labeling of tissue sections (Mikel U V (Ed): Advanced Laboratory Methods in Histology and Pathology. Armed Forces Institute of Pathology, Washington, D.C., USA: 1994), over 100 uterine sections from normoglycemic and diabetic NOD, C57BL/6J or Balb/cJ mice were either probed for MUC1 or IFN-γ. Briefly, deparaffinized sections were rehydrated in a graded series of ethanol, rinsed in 0.01M PBS and were blocked for one hour at room temperature in 5% (w/v) fetal calf serum (FCS) (Fisher BioReagents, Pittsburgh, Pa., USA) in 0.01M PBS containing 0.05% (v/v) Tween-20 and 1% Triton X100. Incubation of uterine sections followed with either CT2 anti-MUC1 antiserum (4 mg/ml) (1:100 dilutions) or with biotinylated monoclonal anti-IFN-γ antibody (1:500) both of which were prepared in 1% FCS in 0.01M PBS. After a brief rinse in two changes of 0.01M PBS CT2-probed sections were incubated at room temperature with Texas Red conjugated goat anti-Armenian hamster antibody (0.8 mg/ml) diluted 1:500 (v/v) in 0.01M PBS containing 1% FCS and nuclei were counterstained with DAPI. IFN-γ localization in labeled uterine sections was visualized with 3,3-Diaminobenzidine tetrahydrochloride (DAB) substrate (Zymed Laboratories Inc., CA, USA), and nuclei were counterstained for one minute in Meyer's hematoxylin (Sigma-Aldrich). Labeled sections were either mounted in a fluorescent mounting medium (Dackocytomation, Mississauga, Ontario, Canada) or in Histomount-mounting medium (Zymed Laboratories Inc., CA, USA). Control sections for MUC1 were incubated overnight at 4° C. with neutralized CT2 anti-MUC1 antiserum as described earlier. HRP-conjugated anti-mouse IgG was used in substitution for IFN-γ in control immunohistochemical staining.

Example 11

Preparation of Uterine Cytosolic and Nuclear Extracts

Using ice-cold sterile glass Dounce-tissue homogenizer, uterine samples collected from virgin and pregnant normoglycemic and diabetic NOD mice were homogenized in 3 volumes of the provided 1× homogenization buffer [Cytosolic and Nuclear Extraction Buffer Kit (Biovision Inc., CA, USA)] as per the manufacturer's instructions. Homogenized samples were centrifuged at 4° C. for 5 minutes at 16,000 g. Supernatants, referred to as cytosolic extracts, were immediately transferred into a clean pre-chilled tube kept on ice. Extraction of nuclear proteins from the remaining insoluble (pellet) fractions followed using ice-cold Nuclear Extraction Buffer Mix according to the supplier's instructions. Protein content of the extracted cytosolic and nuclear fractions was determined by Bradford assay. Extracted protein samples were aliquoted and stored at −80° C. for further analyses.

Example 12

SDS-PAGE and Western Blot (WB) Analysis

Mouse uterine cytosolic and nuclear proteins were resolved on 6 or 8% (w/v) Tris-SDS denaturing polyacrylamide gels in 1× sample loading buffer (150 mM sodium chloride, 1.0% Triton X-100 and 50 mM Tris, pH 8.0). Urea (8M) was added to the Tris-based SDS-PAGE for the detection of MUC1. Protein samples were transferred onto PVDF membranes and blots were probed with appropriate antibodies followed by signal detection using Western heightening-ECL advanced chemiluminescence substrate (PerkinElmer Inc. MA, USA) and exposure on X-OMAT BLUE FILM (PerkinElmer Inc., Canada). Background-corrected intensities of Western blot protein bands on scanned films were processed using Image J. Data were expressed as means±SEM. GAPDH (detected as a band of approximately 37 kDa) was used as an internal loading control.

Example 13

Electron Microscopy (Scanning and Transmission)

Scanning and transmission electron microscopic examinations were performed to assess morphological features of uterine receptivity in implantation sites obtained from normoglycemic and diabetic NOD mice according to the standard protocol (Ryder T. A. Biochem Biophys Res Commun 2002 292:102-108). Implantation site specimens were fixed in 2.5% glutaraldehyde (in 0.01M PBS) and post-fixed for 1 hour at room temperature in 1% aqueous osmium tetroxide. For Scanning electron microscopy, samples were then dehydrated in a graded series of ethanols, critical-point-dried, mounted and coated with gold in a sputter coater (Cressington-108 Auto Fine Coater, Watford, UK) and were examined on Hitachi (S-3400N) scanning electron microscope and images were digitally recorded. For transmission electron microscopy (TEM), samples were fixed as above, processed and embedded in Epon according to the standard protocol (Mikel U V (Ed): Advanced Laboratory Methods in Histology and Pathology. Armed Forces Institute of Pathology, Washington, D.C., USA: 1994). Epon-embedded semi-thin sections (1 μm) were prepared for light microscopic examination to select regions of the implantation sites. Ultra-thin sections were subsequently prepared from the selected regions of implantation sites and counterstained for 10 minutes with 4% aqueous uranyl acetate followed by 2 minutes treatment with lead citrate and viewed on a Hitachi 7000 transmission electron microscope operated at 75 kV.

Example 14

Antibodies

A hamster polyclonal antibody (CT2) directed against the highly conserved domain "SSLSYTNPAVAATSANL"

(SEQ ID NO:1) of the cytoplasmic tail region of human MUC1 was generously provided by Dr. Sandra Gendler (Mayo Clinic, Scottsdale, Ariz., USA). Texas Red-conjugated goat anti-Armenian hamster antibody (SC-2997, Santa Cruz, Calif., USA) was used for immunofluorescent (IF) detection of MUC1. A HPLC-purified (95%) synthetic peptide (SSLSYTNPAVAATSANL) (SEQ ID NO:2) of MUC1 (Sheldon Biotechnology Center, Montreal, Quebec, Canada) was used to neutralize CT2 anti-MUC1 antiserum in preparation of the negative-control sections. Goat polyclonal anti-LIF (N-18, Santa Cruz Biotech., USA), mouse monoclonal anti-GATA3 (B-10, Santa Cruz Biotech.), mouse monoclonal anti-Tbet (4B10, Santa Cruz Biotech.), rabbit anti-mouse anti-NFkBp65 antibody (C-100-4165, Rockland Immunochemicals, PA, USA), rabbit polyclonal anti-phospho-(Ser 536)-NFkBp65 antibody (SC-33020, Santa Cruz Biotech., USA), rabbit polyclonal anti-STAT3 antibody and rabbit polyclonal anti-phospho (Tyr705)-STAT3 antibody (Cell Signalling Technology, MA, USA) were used to examine, respectively, LIF, GATA3, T-bet, NFkBp65, STAT3 expression and/or phosphorylation in WB. Appropriate horse-radish peroxidase (HRP) conjugated secondary antibodies were used in WB detections of all of the above mentioned proteins. Rabbit polyclonal anti-PR antibody (C-19, Santa Cruz Biotech., USA) and mouse monoclonal anti-PIASy antibody (C-11, Santa Cruz Biotech.) were used in WB and in IF analyses. Bovine Texas Red conjugated goat-anti-rabbit (IgG) (Santa Cruz Biotech.) and Alexa fluor488 conjugated goat-anti-mouse antibodies were used, respectively, in double-immunofluorescence detection and co-localization of PR and PIASy. Mouse monoclonal anti-GAPDH (A-3, Santa Cruz Biotech.) and appropriate HRP-conjugated secondary antibodies were used to detect the expression of GAPDH as an internal loading control in WB analysis. Biotinylated monoclonal anti-IFN-γ antibody (clone 1-D1K 1-biotin, Mabtech Inc., USA) was used for immunohistochemical detection of IFN-γ in histological sections. Isotype anti-mouse IgG was substituted for anti-IFN-γ antibody in control sections.

Example 15

Glucose Tolerance Test

Glucose Tolerance Test (GTT): was performed according to standard protocol (Ayala et al 2010). Briefly, basal glucose levels were measured for conscious mice individually caged in 1000 cc plastic mouse caging using a one-touch ultra glucose strips and meter (Acqui-check Aviva, Roche, Montreal, Canada) and approximately 30 microliters of blood obtained via tail venipuncture prior to fasting for six hours in cages equipped with hardwood bedding. Fasting blood glucose was recorded at the end of the six hours fasting period. Mice were then tested for oral glucose tolerance (OGTT) or for insulin sensitivity (Si). For OGTT alert mice were then given 20% D-glucose (2 g/kg body weight) sterile syrup administered orally. For Si experiments mice were given 20% D-glucose (2 g/kg body weight) sterile syrup by intraperitoneal administration through a 1 ml D29 gage "½" insulin syringe (Fisher Scientific, Montreal, Canada). Then after, blood glucose was recorded at 15, 30, 45, 60, 90 and 120 minutes respectively. For Si experiments blood glucose was determined only at 15 minutes. Glucose tolerance graphs were generated by blotting mean±standard error of the mean (SEM) of the recorded glucose data per mouse per minute collection time. One way analysis of variance (ANOVA) followed by student t-test was performed to determine alpha values for statistical differences among mean blood glucose values across experimental mice groups.

Example 16

Insulin ELISA

Fasting immuno-reactive mouse insulin levels were quantitatively determined in citrated platelet-free plasma samples obtained from 6 hours-fasting mice using an Ultrasensitive mouse Insulin Eliza kit (#90080, Crystal chem., IL, USA) according to the manufacturer instructions. Briefly, platelet-free plasma were isolated from freshly obtained citrated whole blood samples of fasting mice and the provided insulin standards were incubated overnight on a shaking platform at 4 C° in a 96 wells plate coated with Guinea pig anti-insulin. Afterwards, unbound sample materials were thoroughly washed with the supplied wash buffers and the bound guinea pig anti-insulin/mouse insulin complex immobilized to the microplate wells were incubated with Horse-radish peroxidase (HRP)-conjugated anti-insulin antibody for 40 minutes at room temperature with continuous agitation. Excess unbound HRP-conjugated anti-insulin antibodies were then washed excessively with wash buffers and the HRP-mediated color reaction was developed with the addition of 3,3',5,5' tetramethylbenzidine (TMB) substrate solution. The amount of insulin (ng/ml) present in the test samples were then measured via interpolation using the standard curve generated by plotting absorbance (at A°450-A°635) versus the corresponding concentration of a wide range (0.1-12.8 ng/ml) of mouse insulin standards according to the provider's instructions. Graphic representation of differences in mean±sem of plasma insulin among different groups of mice were blotted using Prism5 (La Jolla, Calif., USA) software and statistically significant differences (at 95% confidence) were calculated for the different test groups of mice using one way ANOVA followed by Bonferroni modified student t-test comparing differences between individual experimental groups.

Example 17

Calculation of HOMA-IR, HOMA-B and Insulin Sensitivity (Si)

HOMA IR=fasting glucose (mmol/L)×fasting insulin (pg/ml)/22.5 according to the method of Bonora E et al., 2000. Pancreatic β-Cell function (HOMA-B) was calculated according to the method of Tresaco B et al., 2005, HOMA-B=[20×[fasting insulin (ug/mL)×fasting glucose (mmol/L)]−3.5). Insulin sensitivity (Si) was determined according to the method of Matthews D et al., 1985. Si=[basal glucose]−[glucose 15 min]/15).

Example 18

Measurements and Statistical Methods

All data obtained in this study were expressed as mean±standard error and were analyzed by Graph-Pad Prism 5 software (La Jolla, Calif., USA). Statistical differences among all groups of mice were examined by one-way ANOVA followed by Bonferroni's corrections at 95% confidence. Independent one-tailed student t-tests were used to examine differences in peri-implantation loss and % resorption.

What is claimed is:

1. A method for enhancing fertility and/or inhibiting pregnancy failure in an individual in need thereof comprising administering to the individual a composition comprising a macrolide immunosuppressant, wherein said individual has hyperglycemia, impaired fasting glycemia, type 2 diabetes, gestational diabetes, polycystic ovarian syndrome, recurrent miscarriages, is pre-diabetic, is undergoing in vitro fertilization (IVF), and/or is obese.

2. The method of claim 1 wherein the composition inhibits expression of interferon-gamma (IFN-γ) or a downstream IFN-γ-stimulated gene.

3. The method of claim 1 wherein the macrolide immunosuppressant is tacrolimus, pimecrolimus or sirolimus.

4. The method of claim 1 wherein the macrolide immunosuppressant is tacrolimus.

5. The method of claim 1 wherein the macrolide immunosuppressant is administered as a short term, low dose therapy.

6. The method of claim 2 wherein the downstream IFN-γ-stimulated gene is MUC1.

7. The method of claim 1 wherein the individual is undergoing in vitro fertilization (IVF) and administering the composition comprising a macrolide immunosuppressant to the individual increases viable embryo implantation success rate in the individual.

8. The method of claim 1 wherein administration of the composition comprising a macrolide immunosuppressant to the individual in need thereof reduces the risk of intrauterine growth restriction in the individual.

* * * * *

SEQUENCE LISTING

<160> NUMBER OF SEQ ID NOS: 2

<210> SEQ ID NO 1
<211> LENGTH: 17
<212> TYPE: PRT
<213> ORGANISM: Homo sapien

<400> SEQUENCE: 1

Ser Ser Leu Ser Tyr Thr Asn Pro Ala Val Ala Ala Thr Ser Ala Asn
1               5                   10                  15

Leu

<210> SEQ ID NO 2
<211> LENGTH: 17
<212> TYPE: PRT
<213> ORGANISM: Artificial sequence
<220> FEATURE:
<223> OTHER INFORMATION: Synthetic

<400> SEQUENCE: 2

Ser Ser Leu Ser Tyr Thr Asn Pro Ala Val Ala Ala Thr Ser Ala Asn
1               5                   10                  15

Leu